US008076306B2

(12) United States Patent
Monia et al.

(10) Patent No.: US 8,076,306 B2
(45) Date of Patent: Dec. 13, 2011

(54) COMPOSITIONS AND THEIR USES DIRECTED TO HEPCIDIN

(75) Inventors: Brett P. Monia, Encinitas, CA (US); C. Frank Bennett, Carlsbad, CA (US); William A. Gaarde, Carlsbad, CA (US); Trisha Lockhart, Cardiff by the Sea, CA (US); Robert McKay, Poway, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 396 days.

(21) Appl. No.: 11/734,562

(22) Filed: Apr. 12, 2007

(65) Prior Publication Data

US 2007/0275913 A1 Nov. 29, 2007

Related U.S. Application Data

(60) Provisional application No. 60/865,833, filed on Nov. 14, 2006, provisional application No. 60/821,638, filed on Aug. 7, 2006, provisional application No. 60/792,004, filed on Jul. 12, 2006.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. .......... 514/44 A; 435/6; 435/375; 536/23.1; 536/24.1; 536/24.5

(58) Field of Classification Search ........................ None
See application file for complete search history.

(56) References Cited

U.S. PATENT DOCUMENTS

| | | | |
|---|---|---|---|
| 5,801,154 A | 9/1998 | Baracchini et al. | |
| 5,998,148 A * | 12/1999 | Bennett et al. | 435/6 |
| 6,582,908 B2 | 6/2003 | Fodor et al. | |
| 7,169,758 B2 * | 1/2007 | Nicolas et al. | 514/13 |
| 7,411,048 B2 * | 8/2008 | Kulaksiz et al. | 530/387.9 |
| 2001/0053519 A1 | 12/2001 | Fodor et al. | |
| 2003/0228597 A1 | 12/2003 | Cowsert et al. | |
| 2004/0259247 A1 * | 12/2004 | Tuschl et al. | 435/375 |
| 2007/0031844 A1 * | 2/2007 | Khvorova et al. | 435/6 |
| 2007/0275913 A1 | 11/2007 | Monia et al. | |

FOREIGN PATENT DOCUMENTS

WO  WO 02/098444  12/2002
WO  WO 2004/058044  7/2004

OTHER PUBLICATIONS

Bennett et al. Biochimica et Biophysica Acta vol. 1489:19-30, 1999.*
Vickers et al., The Journal of Biological Chemistry vol. 278(9):7108-7118, 2003.*
Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.
Crosby, et al. "Targeting hepcidin with antisense olionucleotides improves anemia endpoints in mice." Blood. vol. 108, No. 11, Part 1, Nov. 2006, pp. 83A-84A.
International Search Report from PCT/US2007/009269, dated Jan. 30, 2008.
New England BioLabs, Inc. Catalogue (1998): 121, 284.
Reynolds et al., Rational siRNA design for RNA interference, Mar. 2004, Nature Biotechnology, vol. 22, pp. 326-330.
Branch et al., "A good antisense molecule is hard to find," TIBS (1998) 23:45-50.
Crooke et al., "Basic Principles of Antisense Therapeutics" Antisense Research and Application (1998) Chapter 1:1-50.
Merle et al. "The Iron Regulatory Peptide Hepcidin Is Expressed in the Heart and Regulated by Hypoxia and Inflammation". Endocrinology 148(6):2663-2668. 2007.
Sanghvi et al., "Heterocyclic Base Modifications in Nucleic Acids and Their Applications in Antisense Oligonucleotides" Antisense Research and Applications (1993) pp. 273-288.
Ilyin et al. "Comparative analysis of mouse hepcidin 1 and 2 genes: evidence for different patterns of expression and co-inducibility during iron overload." FEBS Letters 542 (2003) 22-26.
Gleeson et al. "Hepatic iron metabolism gene expression profiles in HFE associated Hereditary Hemochromatosis." ScienceDirect. Blood Cells, Molecules, and Diseases 38 (2007) 37-44.
Babitt et al. "Bone morphogenetic protein signaling by hemojuvelin regulates hepcidin expression." Nature Genetics. vol. 38, No. 5, May 2006.
Sharma et al. "A role for tumour necrosis factor α in human small bowel iron transport." Biochem. J. (2005) 390, 437-446.
Pak et al. "Suppression of hepcidin during anemia requires erythropoietic activity." Blood, Dec. 1, 2006, vol. 108, No. 12.
Lin et al. "Competitive regulation of hepcidin mRNA by soluble and cell-associated hemojuvelin." Blood, Oct. 15, 2005, vol. 106, No. 8.
Nicolas et al. "Lack of hepcidin gene expression and severe tissue iron overload in upstream stimulatory factor 2 (USF2) knockout mice." PNAS, Jul. 17, 2001, vol. 98, No. 15.
Brett P. Monia, "Targeting Hepcidin with Antisense Oligonucleotides Improves Anemia Endpoints in Mice." Presentation from Dr. Monia, an employee of Isis Pharmaceuticals, Inc. Dec. 2006.
Lee et al. "Regulation of hepcidin transcription by interleukin-1 and interleukin-6." PNAS, Feb. 8, 2005, vol. 102, No. 6 1906-1910.

(Continued)

*Primary Examiner* — Sean McGarry
(74) *Attorney, Agent, or Firm* — Knobbe, Martens, Olson & Bear LLP

(57) ABSTRACT

Disclosed herein are compounds, compositions and methods for modulating the expression of hepcidin in a cell, tissue or animal or preventing, ameliorating or treating anemia. Also provided are methods for prevention, amelioration or treatment of anemia, and for increasing red blood cell count in an animal. Also provided are methods for the prevention, amelioration and/or treatment of low serum iron levels, low red blood cell count and other clinical endpoints of anemia in an animal. These methods may be achieved by administration of compounds or compositions including antisense compounds targeted to a nucleic acid that expresses hepcidin polypeptide combined with an erythropoiesis stimulating agent.

30 Claims, 5 Drawing Sheets

OTHER PUBLICATIONS

Lesbordes-Brion et al. "Targeted disruption of the hepcidin 1 gene results in severe hemochromatosis." Blood, Aug. 15, 2006, vol. 108, No. 4.

Lee et al. "The IL-6 and lipopolysaccharide-induced transcription of hepcidin in HFE-, transferring receptor 2-, and $\beta_2$-microglobulin-deficient hepatocytes." PNAS, Jun. 22, 2004, vol. 101, No. 25, 9263-9265.

Laftah et al. "Effect of hepcidin on intestinal iron absorption in mice." Blood, May 15, 2004, vol. 103, No. 10.

Pigeon et al. "A New Mouse Liver-specific Gene, Encoding a Protein Homologous to Human Antimicrobial Peptide Hepcidin, Is Overexpressed during Iron Overload." The Journal of Biological Chemistry (2001) vol. 276, No. 11, 7811-7819.

Nicolas et al. "The gene encoding the iron regulatory peptide hepcidin is regulated by anemia, hypoxia, and inflammation." The Journal of Clinical Investigation, Oct. 2002, vol. 110, No. 7.

Park et al. "Hepcidin, a Urinary Antimicrobial Peptide Synthesized in the Liver." The Journal of Biological Chemistry (2001) vol. 276, No. 11, 7806-7810.

European Search Report for European Patent Application No. EP 10177775 filed Apr. 12, 2007.

International Search Report and Written Opinion for International Application No. PCT/US2007/009269 filed Apr. 12, 2007.

International Preliminary Report on Patentability for International Application No. PCT/US2007/009269 filed Apr. 12, 2007.

* cited by examiner

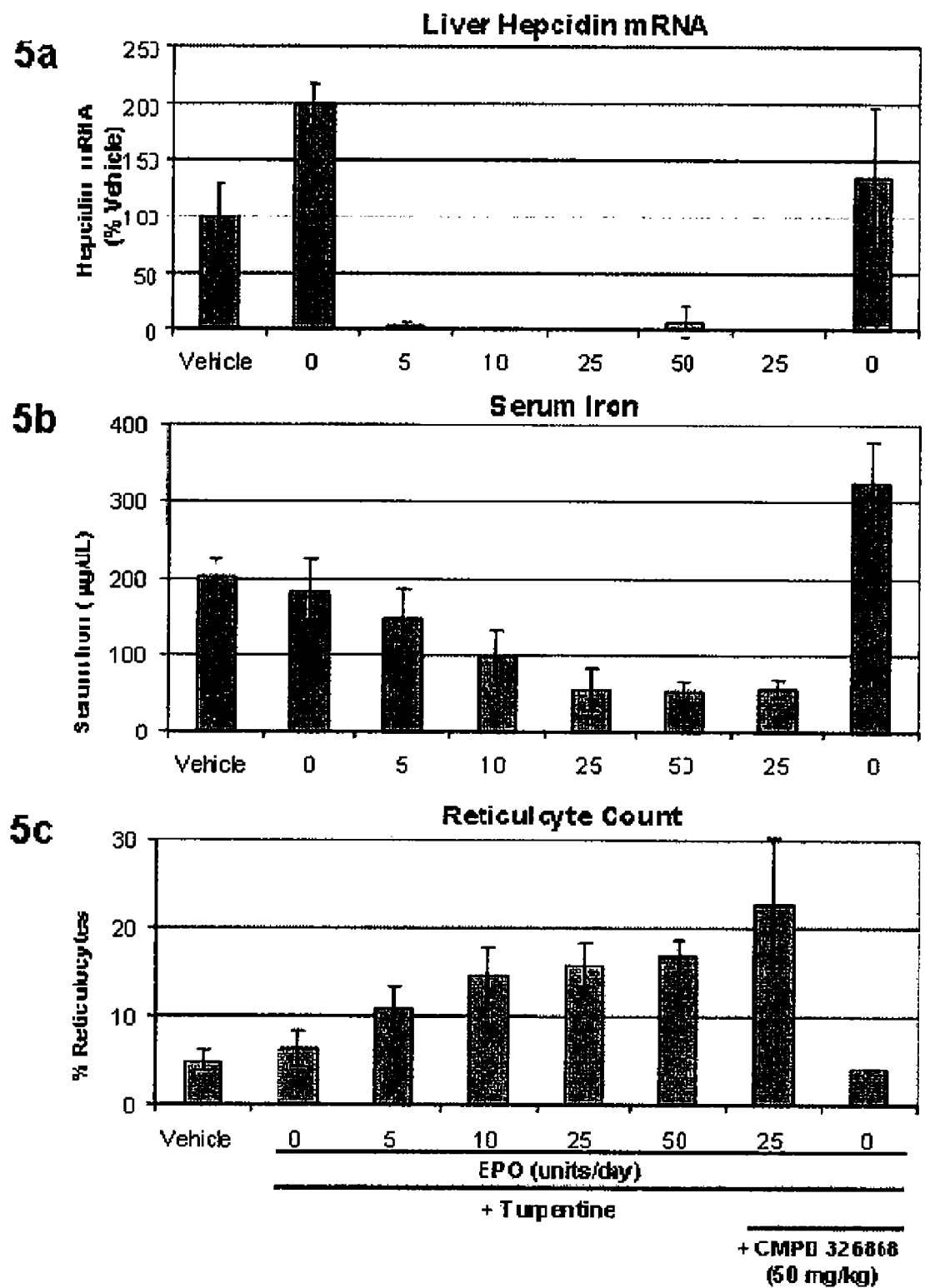
Figure 5 (a, b, and c)

SEQUENCE LISTING

<160> NUMBER OF SEQ ID NOS: 180

<210> SEQ ID NO 1
<211> LENGTH: 588
<212> TYPE: DNA
<213> ORGANISM: Homo sapiens

<400> SEQUENCE: 1

```
gagcctccca cgtggtgtgg atgaggaggc agatggcagg gcctgtgcat ttctgtgctt      60
gagtgggcct tgaaagtggt tcagcaacca ggaagaagtg ttcattcctc gacaacaaca     120
tccccgggct ctggtgactt ggctgacact ggatggccct ggaatgaaaa aggcaaagag     180
gcaaaatgtg caagggccca tctggaacca aggcccata aaagcgactg tcactcggtc      240
ccagacacca gagcaagctc aagacccagc agtgggacag ccagacagac ggcacgatgg     300
cactgagctc ccagatctgg gccgcttgcc tcctgctcct cctcctcctc gccagcctga     360
ccagtggctc tgttttccca caacagacgg gacaacttgc agagctgcaa ccccaggaca     420
gagctggagc cagggccagc tggatgccca tgttccagag gcgaaggagg cgagacaccc     480
acttccccat ctgcattttc tgctgcggct gctgtcatcg atcaaagtgt gggatgtgct     540
gcaagacgta gaacctacct gccctgcccc cgtccctcc cttcctta                   588
```

<210> SEQ ID NO 2
<211> LENGTH: 430
<212> TYPE: DNA
<213> ORGANISM: Homo sapiens

<400> SEQUENCE: 2

```
gactgtcact cggtcccaga caccagagca agctcaagac ccagcagtgg gacagccaga    60
cagacggcac gatggcactg agctcccaga tctgggccgc ttgcctcctg ctcctcctcc   120
tcctcgccag cctgaccagt ggctctgttt tcccacaaca gacgggacaa cttgcagagc   180 tgcaaccccca ggacagagct ggagccaggg ccagctggat gcccatgttc cagaggcgaa   240
ggaggcgaga cacccacttc cccatctgca ttttctgctg cggctgctgt catcgatcaa   300
agtgtgggat gtgctgcaag acgtagaacc tacctgccct gccccgtcc cctcccttcc    360 ttatttattc ctgctgcccc agaacatagg tcttggaata aaatggctgg ttcttttgtt   420
ttccaaaaaa                                                         430

<210> SEQ ID NO 3
<211> LENGTH: 5225
<212> TYPE: DNA
<213> ORGANISM: Homo sapiens

<400> SEQUENCE: 3
atgcctggta gggctggggg ctgctcctgt gtctccccag gtgagcacac ccctattcac    60
tgggccctgc ttcagcctgc agcacccttc aactcccagg agctgggctt gccactctgc   120
tcaccttgtg gagctccatc tgcctttcct ccccaattcc cccactccct gcactcgtct   180
cttcccacaa gagccctgtc tccttttcct agctattccc atctgaggcc atctttattc   240
atttagtttt tagagacagg gtttcactct cacccaggct ggggtgcagt ggcacacaat   300
cacggctcac tgcagccttg accaactaca ggtgcgtagc accacagcca gttttttgta   360
tagatggggt ctcgctttgt tacccaggct gtgacaagag gagcctccca cgtggtgtgg   420
atgaggaggc agatggcagg gcctgtgcat ttctgtgctt gagtgggcct tgaaagtggt   480
tcagcaacca ggaagaagtg ttcattcctc gacaacaaca tccccgggct ctggtgactt   540
ggctgacact ggatggccct ggaatgaaaa aggcaaagag gcaaaatgtg caagggccca   600
tctggaacca aggtttgttg atcccctggg ccgtgtgcac cctgagctgg gcctggtagt   660
ggaaaggaat gaaggcactg cagtcaggca gcctgggttc atcccccagc tagtggtgtc   720
ctaaggaacc ggctccccaa aaacatccct ggcttgtagt gcttgccaat ttctgggtgt   780
caagactccc actgctgctg atttcaggat accagcatga tgccactgaa tgcagagttt   840
cgagatgtgc atggtctgct atgttgagcc aggtctagca taccgctgtg ccctgctgtg   900
ttttagggga gatggggaaa cctggtgggt aagagcaaaa gccctggagt caggctgtcc   960
aggctagaat ctcagctctg cctctggctg agcaagcttg gccatgccc tgatctctgc   1020 cttcagtgcc ttttctgtaa agtgaaggaa atgagtgtcc gacggggagg aggttcctaa  1080
aagggagcag ggtctgggga gcccaggcct ctggggttgg gtgactgaga aggcagcccc  1140
tgaatacaga gcagagctga aggtggggca gtaagtgctg ctgggagaac aggcagcaca  1200
ggctgagttg gtgcagaagt gagtcaacat atgtgccatc gtataaaatg tactcatcgg  1260
actgtagatg ttagctatta ctattactgc tatttttatgt tttatagaca gggtctcact  1320
ctgtcaccca ggctggagtg cagtcacaca atcatagctc actgcaacct cagcctcctg  1380
ggcttaagcg atctgcctca gcctcccaag tagctgggac tacagatgtg tgccaccacg  1440
cctggctaaa tttgtttaaa attttttttg tagagatggg gtctccctat gttgcccagg  1500
ctagtcttga acttctgggc tcaagcgacc ctcctgcctt ggcctcccaa attgctggga  1560
ttacaggcat aagccactgt gctgggccat attactgctg tcatttatgg ccaaaagttt  1620
gctcaaacat tttccagtta ccagagccac atctcaaggg tctgacactg ggaaaacacc  1680
```

```
acgtgcggat cgggcacacg ctgatgcttg ccctgctcag ggctatctag tgttccctgc      1740
cagaacctat gcacgtgtgg tgagagctta aagcaatgga tgcttccccc aacatgccag      1800
acactcctga ggagcctggc ggctgctggc catgccccgt gtgcatgtag gcgatgggga      1860
agtgagtgga ggagagcgga accttgattc tgctcatcaa actgcttaac cgctgaagca      1920
aaagggggaa cttttttccc gatcagcaga atgacatcgt gatggggaaa gggctcccca      1980
gatggctggt gagcagtgtg tgtctgtgac cccgtctgcc ccaccccctg aacacacctc      2040
tgccggctga gggtgacaca ccctgttcc ctgtcgctct gttcccgctt atctctcccg       2100
ccttttcggc gccaccacct tcttggaaat gagacagagc aaaggggagg gggctcagac      2160
caccgcctcc cctggcaggc cccataaaag cgactgtcac tcggtcccag acaccagagc      2220
aagctcaaga cccagcagtg ggacagccag acagacggca cgatggcact gagctcccag      2280
atctgggccg cttgcctcct gctcctcctc ctcctcgcca gcctgaccag tggctctgtt      2340
ttcccacaac aggtgagagc ccagtggcct gggtccttag cagggcagca gggatgggag      2400
agccaggcct cagcctaggg cactggagac acccgagcac tgagcagagc tcaggacgtc      2460
tcaggagtac tggcagctga acaggaacca ggacaggcac ggtggctcat gcctgtaatc      2520
ccagcacttt gggaggttga ggcaggcagc ccacttgagg tcagtttgag accagcctgg      2580
ccaacatggt aaaccccgt ctctactaaa aatacaaaag ttagccaggc ttggtggcag       2640
gtgcctgtaa tcccagctac tcgggagact gaggcaggag aattgcttga cccgcaagg      2700 tggaggttgc acagtgagct gagattgcac cactgcactc cagcctggca acagagcaag      2760
actccatctc caaaaagaa cagaaatcaa tgaagcaccg agtgacaggg actggaaggt       2820
cctaattcca tgggtattta cggaaccct acgccgtgtg gagtcttatt ctagacagtg       2880
gggacgaggc catgaacaag gtagatgaga gaggagattt ctccatcctg gtcagggaat      2940
ttgttaaaga ctgatgaaaa catgaataaa taattgtgtc tagtacattc tattcgtgaa      3000
tctcataaca gacagtggta gagtgaccgt gacccattcg ccacacagta gagtcacttt      3060
tttggtttgt ttttagaga cagggtcttc ctctgttgct gaggctggag tgcagtggtg      3120
cagtcatagt tcactgcagc ctcaacctcc tgtgctcaag caatcctccc acctcagcgt      3180
cccaagtagc tgggacagca ggcacatgcc acgggttggg ggaccacagg catggtcaag     3240
gggctggcag tcaagcaagt gtttcatgag aaagtgacag ttgaccttcg tcttggaggg      3300
tgagagatgg aggcagcaaa gacctaagga gaggacaagc cagcatagcc cagggtcagg     3360
ctgaacaaga ggagatggtg ggacttgggg ataaggctga ggggtgggca gtccctaagt      3420
cttgtgggca accatgcaga cactgatttt tccttggaat aaagaggaag cccccataag      3480
cttttttttt ttttttctgag atagggtctc gctctgtcgt tcaggctggt gtgcagtggc      3540
atcatctggg ctcactgcaa cctccgcctc ccggttcaa gcaattctcc tgcctcagct       3600
tcccgagcag ctgggattac aggcggctgc caccacgccc ggctaatttt tgttttttta      3660
gtagagacag ggtttcacca tgttggccag actggtcttg aactcctgac ctcaggtgat      3720
tctcccacct cggcttccca agtgctggg attacaggcg tgagccactg cgcccagcct       3780
cctgtaggtt tttaaaatgg agaaaaccac aatctcactg ccatgttttt aaaaaactta      3840
atctgccagt caggcaccat ggctcacacc tgtaatccca gagttttggg aggccaaggt      3900
aggaagatca gttgagccca ggagttcaag accagcttgg gcaacacaac cagaccccac     3960
ctctacaaaa aattaaaaaa ttagccgggt gtggtggcgt gcacctgctg tcccagctac      4020
tcgggaagct gaggcgggag catcgcttga gcacaggagg tcaaggctgc agggagctat      4080
```

```
gactgtgcca ctgcactctg gcctgggcaa cagaggaaga ctctgtctaa aaaacaaaca      4140
aaaaaagtga ctctgctgtg tggcaaatgg attgagggc aagaatgcag ggaggtgtgt       4200
taggaggctg gcactggcat ccaggcaggg aaggtgata tcccaaagaa gagtagcagc       4260
tgtggaaaga ggaggaggcg gatctgggag gttttttttt ttaggaaaag ccgcccatgg      4320
gaaggtgagc agaagcaaga aagcaaggcc cctcctaaga gtccatttga gctctgggtt     4380
taaaccactt ggagaggagc aggttgccgg gagccagtct cagaggtcca ctgggccccc     4440
tgccatcctc tgcaccccct tctgctttca cagacgggac aacttgcaga gctgcaaccc    4500
caggacagag ctggagccag ggccagctgg atggtgagcg caacagtgat gcctttccta    4560 gcccctgct ccctccccat gctaaggccg gttccctgct cacattccct tccttcccac       4620
agcccatgtt ccagaggcga aggaggcgag acacccactt ccccatctgc attttctgct     4680
gcggctgctg tcatcgatca aagtgtggga tgtgctgcaa gacgtagaac ctacctgccc     4740
tgcccccgtc ccctcccttc cttatttatt cctgctgccc cagaacatag gtcttggaat     4800
aaaatggctg gttcttttgt tttccaaacc agagtgtctg ttgtcctttc tctctgccga     4860
gtgtctgtgc taagagcttg tcctgaccct gccttgcaag caccagtgct tggtgggtca    4920
tgtggggctg gtgtgtcctg gaggttgcca ggaaagttgg tgaagaaaat ttgtttctgt    4980 tctcccctt catgttgcaa taataggga tgaaagttaa tgtttcctct ccttgagatc       5040
ttcctaaaac agctgtagaa atcagtgcct gtaaggcaag cttgtccaac ctggaggcca   5100
catgcagccc tggatggctt tgaatgcacc caacacaaat ttgtagtttc ttaaggcatt    5160
atgagatttt tccgcaattt ttttttttct catcagctgt cattagtgtt agtgtgtttt    5220
atgtg                                                                5225

<210> SEQ ID NO 4
<211> LENGTH: 410
<212> TYPE: DNA
<213> ORGANISM: Mus musculus

<400> SEQUENCE: 4
agtccttaga ctgcacagca gaacagaagg catgatggca ctcagcactc ggacccaggc       60
tgcctgtctc ctgcttctcc tccttgccag cctgagcagc accacctatc tccatcaaca     120
gatgagacag actacagagc tgcagccttt gcacgggaa gaaagcaggg cagacattgc     180
gataccaatg cagaagagaa ggaagagaga caccaacttc cccatctgca tcttctgctg    240
taaatgctgt aacaattccc agtgtggtat ctgttgcaaa acatagccta gagccacatc     300
ctgacctctc tacaccccctg cagccccctca acccccattat ttattcctgc cctccccacc    360
aatgaccttg aaataaagac gatttatttt tcaaaaaaaa aaaaaaaaa                  410

<210> SEQ ID NO 5
<211> LENGTH: 2449
<212> TYPE: DNA
<213> ORGANISM: Mus musculus

<400> SEQUENCE: 5
gacattgctg ggtccttctg agaaacccag tgagtaacag ccatactgaa ggcactgata      60
ggggtaaagg tacagttctt ccactcacca atccaatcac tgtttagggg aaagaagggg    120
aatttttctg agagccacag tgtgacatca caggtggctg gctgcaggct tgtgtccctg     180
gttctgtctg ccccacctc tggatgcacc tctgctggct gtaggtgaca caaccctgtc     240
ccctgtcact gttcccgctt atctctcccg cctgtttggc gccactattt tcttggaaat   300
```

```
gagtcagagc aaaatggggg tgggtgaggc gcaggtgacc ctcccctacc actagtccca    360
taaaaaggac tgggactggc tcctagacag ccaccacaca agtccttaga ctgcacagca    420
gaacagaagg catgatggca ctcagcactc ggacccaggc tgcctgtctc ctgcttctcc    480
tccttgccag cctgagcagc accacctatc tccatcaaca ggtgagcacc ccaggcccat    540
tgtggtggga gagccaggtc ccaggcaggc aggagctgct caccactgag tagttagaat    600
ggctcaggag tgatggcagc tgctgacaag gaagagggtg gtccttagtg ggagctggga    660
agctgcacag gtgtccttga atagctactc tgttgtccta ctgtggaaaa tgaagcatgg    720
tgggagccaa acaaaagtgt tccttggctg tcccacccct tcagggcatt ctttaagcag    780
cctttacatg agtattttat aagaattac tgtggatagt acaaaagaca atgggcagaa    840
aaactctaat gaggaaggac cagaggtggg gctaagaggc tgacagccag gcaaagtatt    900
ctatgagaaa atgatacaga agtcgggcag tggtggcaca tgcctttaat cccagcattt    960
gggaggcaga ggcaggtgga tttctgagtt tgaatccagc ctggtctaca aagtgagttt   1020
caagacagcc agggctacac agagaaatcc tgtctgaaaa aaaaaaaaaa acaaaaaaag   1080
aaaaaaaaaa tgatacagaa gggtctggag agatggctta gctgttagga acatttgatg   1140
cttgtgcata ggacctagag tcagttccca gcacccatgt ggtggatcac aaccatcctg   1200
aactctactt ccagggtacc tgatgccttc tgccctagat ggcagtcagc agtaagcatg   1260
catatgatac acataggcac tcaaggcaat cacaagaccc ttggggactg tagggtctga   1320
taagtgaagc cagtgttggc aataaagggc tgtagaggtt ctgctgtgcc gagctttgtg   1380
gacagctgtg cagatgatga tctgtcctgg aaagccacaa tccagatgaa tgtgctataa   1440
gcctttgtgc tatggggtga cctggttata agagataaga tgcagggaaa actgtccgga   1500
gtgtgcaaaa gcaaagaaaa gtgggtgctt ttaggagcat ccaaggaatg gtgaggggac   1560
acagggcagt aggagcccct tctagaaatt ctgtctaagc acagtcccta aatctctggg   1620
gagaagctgg cagagaaaag tcaggaagct atgccgggta ctccacaaga ttcaatacct   1680
cttctgcttt cacagatgag acagactaca gagctgcagc ctttgcacgg ggaagaaagc   1740
agggcagaca ttgcggtaag agcatctggg actccctccc tgatccccag cctctcccat   1800
gcccaagcta ggctgcttac ctctctttct ttacacagat accaatgcag aagagaagga   1860
agagagacac caacttcccc atctgcatct tctgctgtaa atgctgtaac aattcccagt   1920
gtggtatctg ttgcaaaaca tagcctagag ccacatcctg acctctctac accctgcag   1980
cccctcaacc ccattattta ttcctgccct ccccaccaat gaccttgaaa taaagacgat   2040
tttatttca aacctaggtg tctaggtttt ttacccttt tttttcttgc caaagaaatg    2100
gactttttgc aagccctgct gaggacaggc actgagctgg gtttacaggt ctatgtacaa   2160
tgaggctgct ggaacgctgg ggaacagcat ttcttgtctg ttcttcactt tgcttcttat   2220
ttcaaaagat ctggagttta tgtagcagcc tggaaggaac ctgaaaagac tttccttagt   2280
cttttctgt ctttcattct tcttaaagt tttttacaaa tgtgtgtatg catgtgtgtg    2340
tgtgtgtgtg tgtgtgtgtg agagagagag cacatggaag agccagagta gccccagctg   2400
atatgaaact tgctttgtca aactcagaga tcatttgcct ttgccttct               2449
```

<210> SEQ ID NO 6
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 6
aggaggcgag acacccactt                                           20

<210> SEQ ID NO 7
<211> LENGTH: 22
<212> TYPE: DNA
<213> ORGANISM: Artificial Sequence
<220> FEATURE:
<223> OTHER INFORMATION: Oligomeric Compound

<400> SEQUENCE: 7
tcccacactt tgatcgatga ca                                        22

<210> SEQ ID NO 8
<211> LENGTH: 24
<212> TYPE: DNA
<213> ORGANISM: Artificial Sequence
<220> FEATURE:
<223> OTHER INFORMATION: Oligomeric Compound

<400> SEQUENCE: 8
catctgcatt ttctgctgcg gctg                                      24

<210> SEQ ID NO 9
<211> LENGTH: 24
<212> TYPE: DNA
<213> ORGANISM: Artificial Sequence
<220> FEATURE:
<223> OTHER INFORMATION: Oligomeric Compound

<400> SEQUENCE: 9
tgcagaagag aaggaagaga gaca                                      24

<210> SEQ ID NO 10
<211> LENGTH: 24
<212> TYPE: DNA
<213> ORGANISM: Artificial Sequence
<220> FEATURE:
<223> OTHER INFORMATION: Oligomeric Compound

<400> SEQUENCE: 10
cacactggga attgttacag catt                                      24

<210> SEQ ID NO 11
<211> LENGTH: 28
<212> TYPE: DNA
<213> ORGANISM: Artificial Sequence
<220> FEATURE:
<223> OTHER INFORMATION: Oligomeric Compound

<400> SEQUENCE: 11
caacttcccc atctgcatct tctgctgt                                  28

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
aatgcacagg ccctgccatc                                           20

<210> SEQ ID NO 13
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 13
cacagaaatg cacaggccct                                               20

<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 14
tcaagcacag aaatgcacag                                               20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
cccactcaag cacagaaatg                                               20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
caaggcccac tcaagcacag                                               20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
actttcaagg cccactcaag                                               20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18
gctgaaccac tttcaaggcc                                               20

<210> SEQ ID NO 19
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 19
tggttgctga accactttca                                               20
```

<210> SEQ ID NO 20
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 20
gaggaatgaa cacttcttcc                                              20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
ttgtcgagga atgaacactt                                              20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
tgttgttgtc gaggaatgaa                                              20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
ccaagtcacc agagcccggg                                              20

<210> SEQ ID NO 24
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 24
gtcagccaag tcaccagagc                                              20

<210> SEQ ID NO 25
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 25
ccagtgtcag ccaagtcacc                                              20

<210> SEQ ID NO 26
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 26
gccatccagt gtcagccaag                                            20

<210> SEQ ID NO 27
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 27
ccagggccat ccagtgtcag                                            20

<210> SEQ ID NO 28
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 28
tcattccagg gccatccagt                                            20

<210> SEQ ID NO 29
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 29 cttttttcatt ccagggccat                                           20

<210> SEQ ID NO 30
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 30
ggcccttgca cattttgcct                                            20

<210> SEQ ID NO 31
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 31
ccagatgggc ccttgcacat                                            20

<210> SEQ ID NO 32
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 32
tggttccaga tgggcccttg                                            20

<210> SEQ ID NO 33
<211> LENGTH: 20
```

-continued

```
<212> TYPE: DNA
<213> ORGANISM: Artificial Sequence
<220> FEATURE:
<223> OTHER INFORMATION: Oligomeric Compound

<400> SEQUENCE: 33
ggccttggtt ccagatgggc                                               20

<210> SEQ ID NO 34
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 34
gtgacagtcg cttttatggg                                               20

<210> SEQ ID NO 35
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 35
accgagtgac agtcgctttt                                               20

<210> SEQ ID NO 36
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 36
ctgggaccga gtgacagtcg                                               20

<210> SEQ ID NO 37
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 37
cagggcaggt aggttctacg                                               20

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
tgtctgggac cgagtgacag                                               20

<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
tctggtgtct gggaccgagt                                               20
```

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
ctgggagctc agtgccatcg                                                    20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
cagatctggg agctcagtgc                                                    20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
agagccactg gtcaggctgg                                                    20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
aaaacagagc cactggtcag                                                    20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
gtgggaaaac agagccactg                                                    20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
gctctgcaag ttgtcccgtc                                                    20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 46
ttgcagctct gcaagttgtc                                              20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
ggaacatggg catccagctg                                              20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
cctctggaac atgggcatcc                                              20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
ggaagtgggt gtctcgcctc                                              20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
cagcagaaaa tgcagatggg                                              20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
gcagccgcag cagaaaatgc                                              20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
tgacagcagc cgcagcagaa                                              20

<210> SEQ ID NO 53
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 53
atcgatgaca gcagccgcag                                              20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
cacactttga tcgatgacag                                              20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
catcccacac tttgatcgat                                              20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
cagcacatcc cacactttga                                              20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
tcttgcagca catcccacac                                              20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
ttattccaag acctatgttc                                              20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
cagccatttt attccaagac                                              20
```

```
<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
agaaccagcc attttattcc                                                   20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
acaaaagaac cagccatttt                                                   20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
cctgaccagg atggagaaat                                                   20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
caaattccct gaccaggatg                                                   20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
tttaacaaat tccctgacca                                                   20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
cagtctttaa caaattccct                                                   20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 66
gttttcatca gtctttaaca                                            20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
tagacacaat tatttattca                                            20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
tgtactagac acaattattt                                            20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
tagaatgtac tagacacaat                                            20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
attcacgaat agaatgtact                                            20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
atgagattca cgaatagaat                                            20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
atgggtcacg gtcactctac                                            20

<210> SEQ ID NO 73
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 73
ggcgaatggg tcacggtcac                                              20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
tgtgtggcga atgggtcacg                                              20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
cagccccttg accatgcctg                                              20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
tgtcactttc tcatgaaaca                                              20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
tccaagacga aggtcaactg                                              20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
ttgttcagcc tgaccctggg                                              20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
ttatccccaa gtcccaccat                                              20
```

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
cctcagcctt atccccaagt                                              20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
tagggactgc ccaccectca                                              20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
ctgcatggtt gcccacaaga                                              20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
agtgtctgca tggttgccca                                              20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
aaatcagtgt ctgcatggtt                                              20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
aggaaaaatc agtgtctgca                                              20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
tccattttaa aaacctacag                                          20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
gccagtgaga ttgtggtttt                                          20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
acatggccag tgagattgtg                                          20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
ggcatccagc tggccctggc                                          20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
tgctgtgcag tctaaggact                                          20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
tgttctgctg tgcagtctaa                                          20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
cttctgttct gctgtgcagt                                          20

<210> SEQ ID NO 93
<211> LENGTH: 20

```
<212> TYPE: DNA
<213> ORGANISM: Artificial Sequence
<220> FEATURE:
<223> OTHER INFORMATION: Oligomeric Compound

<400> SEQUENCE: 93
catgccttct gttctgctgt                                               20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
atcatgcctt ctgttctgct                                               20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
gtgccatcat gccttctgtt                                               20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
gagtgccatc atgccttctg                                               20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
gctgagtgcc atcatgcctt                                               20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
gtgctgagtg ccatcatgcc                                               20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
cgagtgctga gtgccatcat                                               20
```

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
gggtccgagt gctgagtgcc                                              20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
gcctgggtcc gagtgctgag                                              20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
ggcagcctgg gtccgagtgc                                              20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
agacaggcag cctgggtccg                                              20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
gcaggagaca ggcagcctgg                                              20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
ctggcaagga ggagaagcag                                              20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 106
ctgctcaggc tggcaaggag                                            20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
ggtgctgctc aggctggcaa                                            20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
gtggtgctgc tcaggctggc                                            20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
aggtggtgct gctcaggctg                                            20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
taggtggtgc tgctcaggct                                            20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
ataggtggtg ctgctcaggc                                            20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
gataggtggt gctgctcagg                                            20

<210> SEQ ID NO 113
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 113
tgatggagat aggtggtgct                                               20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
ttgatggaga taggtggtgc                                               20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
atctgttgat ggagataggt                                               20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
catctgttga tggagatagg                                               20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
tctgtctcat ctgttgatgg                                               20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
tagtctgtct catctgttga                                               20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
gtagtctgtc tcatctgttg                                               20
```

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
gctctgtagt ctgtctcatc                                               20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
gcagctctgt agtctgtctc                                               20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
gctgcagctc tgtagtctgt                                               20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
aaggctgcag ctctgtagtc                                               20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
gtgcaaaggc tgcagctctg                                               20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
ttccccgtgc aaaggctgca                                               20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound -continued

<400> SEQUENCE: 126
tttcttcccc gtgcaaaggc                                           20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
tgctttcttc cccgtgcaaa                                           20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
atgtctgccc tgctttcttc                                           20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
gcattggtat cgcaatgtct                                           20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
ttctgcattg gtatcgcaat                                           20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
tctcttctgc attggtatcg                                           20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
aagttggtgt ctctcttcct                                           20

<210> SEQ ID NO 133
<211> LENGTH: 20

```
<212> TYPE: DNA
<213> ORGANISM: Artificial Sequence
<220> FEATURE:
<223> OTHER INFORMATION: Oligomeric Compound

<400> SEQUENCE: 133
gggaagttgg tgtctctctt                                            20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
tttacagcag aagatgcaga                                            20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
agcatttaca gcagaagatg                                            20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
acagcattta cagcagaaga                                            20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
ttacagcatt tacagcagaa                                            20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
aattgttaca gcatttacag                                            20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
tgggaattgt tacagcattt                                            20
```

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
cactgggaat tgttacagca                                               20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
gataccacac tgggaattgt                                               20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
aacagatacc acactgggaa                                               20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
gcaacagata ccacactggg                                               20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
tttgcaacag ataccacact                                               20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
gttttgcaac agataccaca                                               20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

```
<400> SEQUENCE: 146
tatgttttgc aacagatacc                                              20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
gctctaggct atgttttgca                                              20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
ggtcaggatg tggctctagg                                              20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
gagaggtcag gatgtggctc                                              20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
tagagaggtc aggatgtggc                                              20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151
gtgtagagag gtcaggatgt                                              20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
agggcaggaa taaataatgg                                              20

<210> SEQ ID NO 153
<211> LENGTH: 20
```

```
<212> TYPE: DNA
<213> ORGANISM: Artificial Sequence
<220> FEATURE:
<223> OTHER INFORMATION: Oligomeric Compound

<400> SEQUENCE: 153
ggagggcagg aataaataat                                            20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
atttcaaggt cattggtggg                                            20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
ttatttcaag gtcattggtg                                            20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
cgtctttatt tcaaggtcat                                            20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
aaaatcgtct ttatttcaag                                            20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
ataaaatcgt ctttatttca                                            20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
aaataaaatc gtctttattt                                            20
```

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
gggtgctcac ctgttgatgg                                          20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
tgcttactgc tgactgccat                                          20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
atgcatgctt actgctgact                                          20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
gcctatgtgt atcatatgca                                          20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
cagcagaacc tctacagccc                                          20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
tctgtctcat ctgtgaaagc                                          20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
atgctcttac cgcaatgtct                                           20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
gcattggtat ctgtgtaaag                                           20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
ccttccctga aggttcctcc                                           20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
gctcatagaa ctgtcaggct                                           20

<210> SEQ ID NO 170
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 170
ggtcaggatg tggct                                                15

<210> SEQ ID NO 171
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 171
caggatgtgg ctcta                                                15

<210> SEQ ID NO 172
<211> LENGTH: 12
<212> TYPE: DNA
<213> ORGANISM: Artificial Sequence
<220> FEATURE:
<223> OTHER INFORMATION: Oligomeric Compound

<400> SEQUENCE: 172
gtcaggatgt gg                                                   12

<210> SEQ ID NO 173
<211> LENGTH: 36

```
<212> TYPE: DNA
<213> ORGANISM: Artificial Sequence
<220> FEATURE:
<223> OTHER INFORMATION: Oligomeric Compound

<400> SEQUENCE: 173
gagaggtcag gatgtggctc taggctatgt tttgca                              36

<210> SEQ ID NO 174
<211> LENGTH: 28
<212> TYPE: DNA
<213> ORGANISM: Artificial Sequence
<220> FEATURE:
<223> OTHER INFORMATION: Oligomeric Compound

<400> SEQUENCE: 174
gtcaggatgt ggctctaggc tatgtttt                                       28

<210> SEQ ID NO 175
<211> LENGTH: 23
<212> TYPE: DNA
<213> ORGANISM: Artificial Sequence
<220> FEATURE:
<223> OTHER INFORMATION: Oligomeric Compound

<400> SEQUENCE: 175
tgtggctcta ggctatgttt tgc                                            23

<210> SEQ ID NO 176
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
ggtcaggatg tggctcaagg                                                20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
ggtcaggaag tggctctagg                                                20

<210> SEQ ID NO 178
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
ggtcagtttg tggctctagg                                                20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
ggtgaggatg tggctccagg                                                20
```

```
<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
ggtctggatg tgcctctcgg                                                    20
```

COMPOSITIONS AND THEIR USES DIRECTED TO HEPCIDIN

SEQUENCE LISTING

The present application is being filed along with a Sequence Listing in electronic format. The Sequence Listing is provided as a file entitled BIOL0082USSEQ.txt, created on Apr. 12, 2007 which is 42 Kb in size. The information in the electronic format of the sequence listing is incorporated herein by reference in its entirety.

BACKGROUND OF THE INVENTION

Anemia is characterized by a lower than normal number of red blood cells (erythrocytes) in the blood, usually measured by a decrease in the amount of hemoglobin. The cause of anemia can include chronic inflammation, chronic kidney disease, kidney dialysis treatment, genetic disorders, chronic infection, acute infection, cancer and cancer treatments. Altered iron homeostasis and/or erythropoiesis in these conditions can result in decreased erythrocyte (red blood cell) production. Anemia can limit the use of chemotherapeutic agents during cancer treatment. Symptoms of anemia include fatigue, pallor and poor exercise tolerance. Though rarely life threatening, anemia can be severely debilitating and difficult to treat. Clinical signs of anemia include low serum iron (hypoferremia), low hemoglobin levels, low hematocrit levels, decreased red blood cells, decreased reticulocytes, increased soluble transferrin receptor and iron restricted erythropoesis.

In some cases, increasing dietary iron or intravenous iron delivery are used to treat anemia. Erythropoietin (EPO) stimulates erythroprogenitors and promotes red blood cell formation. Recombinant erythropoietin and other erythropoiesis stimulating agents (ESAs) are used for treating anemia, although certain patients respond poorly to this treatment. EPO is well known and is commercially available through Amgen (Thousand Oaks, Calif.).

Anemia of chronic disease (ACD) is a highly prevalent, inflammatory-driven disorder that is poorly treated with currently available therapies. The mechanism underlying ACD is chronic inflammation, which results in changes in iron homeostasis and utilization, resulting in a blunting of erythroid progenitor cell proliferation and red cell function.

ACD is associated with increased production of inflammatory cytokines, including, for example, tumor necrosis factor-.alpha., IL-1.beta., IL-6, and interferon-.gamma. (Means (1995) Stem cells 13:32-37 and Means (1999) Int J Hematol 70:7-12). In several in vitro and in vivo animal model systems, inflammatory cytokines negatively affected the ability to mediate erythropoietin (EPO) production, EPO responsiveness, and the coordinate regulation of iron metabolism (Roodman et al. (1989) Adv Exp Med Biol 271:185-196; Fuchs et al. (1991) Eur J Hematol 46:65-70; Jelkmann et al. (1994) Ann NY Acad Sci 718:300-311; Vannucchi et al. (1994) Br J Hematol 87:18-23; and Oldenburg et al. (2001) Aliment Pharmacol Ther 15:429-438). Administration of EPO failed to reverse anemia in mice continuously exposed to TNF-.alpha. (Clibon et al. (1990) Exp Hematol 18:438-441). Increased levels of inflammatory cytokines, such as TNF-.alpha., IL-1.beta., and INF-.gamma., contribute to defective EPO production and EPO resistance observed in patients with anemia of chronic disease (Jelkmann et al. (1991) Ann NY Acad Sci 718:300-311 and Macdougall and Cooper (2002) Neprol Dial Transplant 17(11):39-43.). Therefore, various cytokines, e.g., inflammatory cytokines and cytokines associated with inflammation, are involved in many aspects of the pathogenesis of anemia of chronic disease, including inhibition of erythroid progenitors, inhibition of EPO production, and impairment of iron release and iron availability for erythropoiesis.

Hepcidin is an 8 kD polypeptide that is produced by hepatocytes in response to inflammation or to rising levels of iron in the blood. The primary role of hepcidin is to regulate blood iron levels by facilitating a decrease in these blood iron levels. Hepcidin binds with and down regulates ferroportin to reduce ferroportin mediated release of iron into the blood. Hepcidin expression is increased in conditions of acute and chronic inflammation resulting in decreased iron availability for erythropoeisis. Hepcidin is frequently measured in the urine or serum as a biomarker of anemia status. (Ganz et al. (2006) Am J Physiol Gastrointest Liver Physiol 290:G199-G203; and Ganz (2003) Blood 102(3):783-788). Moreover, hepcidin over expression has been strongly linked to ACD mechanistically as a mediator of this disorder in animal models and in humans.

SUMMARY OF THE INVENTION

Provided herein are compounds, particularly oligomeric compounds, especially nucleic acid and nucleic acid-like oligomers, which are targeted to a nucleic acid encoding hepcidin. Preferably, the oligomeric compounds are antisense compounds targeted to a nucleic acid molecule encoding hepcidin, particularly human hepcidin (GenBank Accession Nos. BM719679.1, entered Mar. 1, 2002; NM_021175.2, entered Jul. 23, 2004; and nucleotides 7819907 to 7825131 of NT_011196.11, entered Jan. 5, 2003; all herein incorporated by reference and assigned SEQ ID NOS: 1, 2 and 3, respectively), that modulate the expression of hepcidin. In a particular embodiment, the antisense compounds are antisense oligonucleotides. In another embodiment, the antisense compounds are siRNAs. In one embodiment, the compounds comprise at least an 8 nucleobase portion, preferably at least a 12 nucleobase portion, more preferably at least a 15 nucleobase portion, of the sequences listed in Table 3. In a further embodiment, the compounds are at least 80% identical to the sequences listed in or below Table 3.

Herein, active target segments are identified for SEQ ID NOS: 1, 2 and 3. A series of antisense oligonucleotide compounds was designed to target one or more of SEQ ID NOS: 1, 2, and 3. Active target segments were then identified as being regions of the hepcidin mRNA associated with the most active antisense oligonucleotides. Compounds are provided that are targeted to an active target segment of SEQ ID NO: 1, 2, or 3 and modulate the expression of hepcidin. In one embodiment, the compounds comprise at least an 8 nucleobase portion, preferably at least a 12 nucleobase portion, more preferably at least a 15 nucleobase portion, that is complementary to an active target segment. In a further embodiment, the compounds are at least 80% complementary to an active target segments. In another embodiment, the compounds are 13 to 30 nucleobases in length. In another embodiment, the compounds are at least about 80% complementary to at least a 20 nucleobase portion of the active target segment. In yet another embodiment, the compounds are complementary to at least an 8 nucleobase portion of the active target segment.

In another aspect, the compounds comprise at least one modified internucleoside linkage, modified sugar moiety, or modified nucleobase. In another aspect, the compounds comprise a chimeric oligonucleotide. In one aspect, the compounds comprise a phosphorothioate linkage. In another aspect, the compounds comprise a 2'-MOE modification. In another aspect, the compounds comprise a 5-methylcytosine modification.

Another embodiment provides for a composition comprising erythropoietin and an antisense compound targeted to a nucleic acid encoding hepcidin. In one aspect, the compound is an antisense oligonucleotide targeted to a nucleic acid molecule encoding hepcidin A further embodiment provides methods for prevention, amelioration or treatment of anemia in an individual comprising administering to the individual erythropoietin and an antisense compound targeted to an nucleic acid encoding hepcidin. In one aspect, the compound is an antisense oligonucleotide targeted to a nucleic acid molecule encoding hepcidin.

In one embodiment, the antisense oligonucleotide used in this method causes an increase in serum iron levels, prevention of iron restriction of erythropoiesis, or a combination thereof. In yet another embodiment, the administration causes an increase in red blood cell counts, reticulocyte counts, hemoglobin levels, hematocrit levels, or a combination thereof.

In one aspect, the cause of anemia is chronic inflammation, chronic kidney disease, kidney dialysis treatment, genetic disorders, chronic infection, acute infection, cancer, or cancer treatments. In another aspect, the anemia is associated with inflammation. In another aspect, it is anemia of chronic disease (ACD).

In another embodiment, the individual receiving the administration has received or has been continuously receiving erythropoietin prior to treatment. Another embodiment provides methods for prevention, amelioration or treatment of anemia in an individual who is being treated with erythropoietin comprising administering to the individual erythropoietin and an antisense oligonucleotide targeted to a nucleic acid molecule encoding hepcidin.

In another embodiment, the administration comprises delivery of the antisense oligonucleotide and erythropoietin in a single formation. In one aspect, the delivery of the single formulation is by injection. In another embodiment, the administration comprises delivery of the antisense oligonucleotide and erythropoietin in separate formulations. In one aspect delivery of separate formulations is by injection. In another aspect, separate formulations are delivered at distinct timepoints. In another aspect, they are delivered simultaneously.

Another embodiment provides a method for increasing red blood cell count in an animal that is being treated with erythropoietin comprising administering to the animal an oligomeric compound targeted to a nucleic acid encoding hepcidin. In one aspect, the compound is an antisense oligonucleotide targeted to a nucleic acid molecule encoding hepcidin.

Another embodiment provides a method for increasing red blood cell count in an animal comprising the steps of delivering an erythropoietin therapy and delivering an antisense oligonucleotide therapy targeted to a nucleic acid molecule encoding hepcidin.

Another embodiment provides methods for prevention, amelioration or treatment of anemia in an individual comprising administering to the individual antisense compound targeted to an nucleic acid encoding hepcidin, wherein the individual is further receiving erythropoietin therapy. In one aspect, the erythropoietin therapy had occurred or was continuously occurring at the time of administration of the antisense oligonucleotide. In another aspect the individual is therapy naïve, meaning that the individual had not before received or was not receiving erythropoietin therapy at the initiation of the method. In one embodiment, the method further comprises administering to the individual erythropoietin. In one embodiment, the antisense compound and erythropoietin are administered in a single formulation. In another embodiment, they are administered in separate formulations. In one embodiment, the separate formulations are administered simultaneously. In another aspect the separate formulations are administered at distinct times. In one aspect, the formulations are administered by injection.

Another embodiment provides methods for increasing red blood cells in an individual antisense compound targeted to an nucleic acid encoding hepcidin, wherein the individual is further receiving erythropoietin therapy. In one aspect, the erythropoietin therapy had occurred or was continuously occurring at the time of administration of the antisense oligonucleotide. In another aspect the individual is therapy naïve, meaning that the individual had not before received or was not receiving erythropoietin therapy at the initiation of the method. In one embodiment, the method further comprises administering to the individual erythropoietin. In one embodiment, the antisense compound and erythropoietin are administered in a single formulation. In another embodiment, they are administered in separate formulations. In one embodiment, the separate formulations are administered simultaneously. In another aspect the separate formulations are administered at distinct times. In one aspect, the formulations are administered by injection.

Also provided herein are methods for providing a combination therapy for prevention, treatment or amelioration of anemia or increasing red blood cells in an animal comprising the step of administering to the animal an antisense compound disclosed herein, wherein the animal is further receiving erythropoietin therapy. In one embodiment, the animal has been receiving erythropoietin therapy prior to the administration of the antisense compound. In another embodiment the animal begins erythropoietin therapy simultaneously with the administration of the antisense compound. In one embodiment, the combination therapy comprises receiving the antisense compound and an erythropoietin therapy compound in a single formulation. In another embodiment, the combination therapy comprises receiving the antisense compound and an erythropoietin therapy compound in separate formulations. In one embodiment, recombinant human erythropoietin is administered as the erythropoietin therapy.

Also provided herein is a use of an oligomeric compound targeted to a nucleic acid encoding hepcidin for the preparation of a medicament for the prevention, amelioration, and/or treatment of anemia. In one aspect, the compound is an antisense oligonucleotide targeted to a nucleic acid encoding hepcidin. Another embodiment provides for the use of an oligomeric composition targeted to a nucleic acid encoding hepcidin for the preparation of a medicament for the prevention, amelioration, and/or treatment of anemia. In one aspect the composition comprises an antisense oligonucleotide targeted to a nucleic acid encoding hepcidin and erythropoietin. In one aspect, the medicament is prepared for treatment of anemia in a patient being treated with erythropoietin. In one aspect, the cause of anemia is chronic inflammation, chronic kidney disease, kidney dialysis treatment, genetic disorders, chronic infection, acute infection, cancer or cancer treatments. In another embodiment, the anemia is anemia of chronic disease (ACD). In one embodiment, the medicament is formulated for delivery by injection.

BRIEF DESCRIPTION OF THE FIGURES

FIG. 5 (a-c). Graphs illustrating the enhanced reticulocyte counts in turpentine-treated mice receiving erythropoietin and an antisense oligonucleotide targeted to hepcidin.

DETAILED DESCRIPTION OF THE INVENTION

Figure 1:
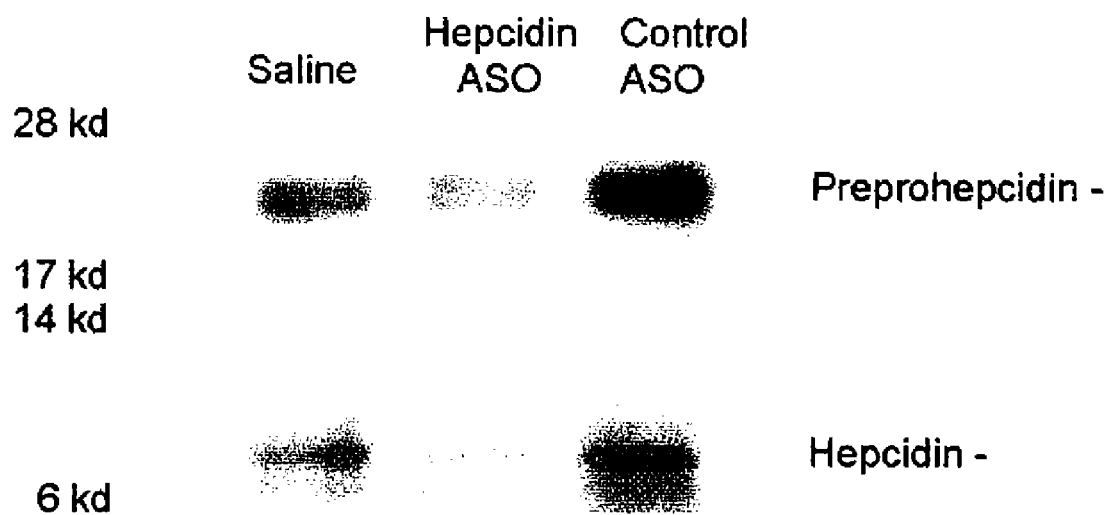
FIG. 1. Western blot of liver lysate following treatment with antisense oligonucleotides targeting hepcidin mRNA and showing that the hepcidin polypeptide is reduced following treatment. Hepcidin was detected with hepcidin antibody (Alpha Diagnostics, HEPC11-A, 0.3.micro.g/ml).

Anemia is a severely debilitating condition stemming from a lower than normal number of red blood cells (erythrocytes) in the blood that characterizes a number of diseases and conditions. Therapeutic interventions for these diseases or conditions are not completely satisfactory due to lack of efficacy and/or unwanted side effects of the compounds. Provided herein are methods, uses, compositions and compounds for the prevention, amelioration, and/or treatment of anemia. As used herein, the term "prevention" means to delay or forestall onset or development of a condition or disease for a period of time from hours to days, preferably weeks to months. As used herein, the term "amelioration" means a lessening of at least one indicator of the severity of a condition or disease. By way of example, some appropriate indicators include low serum iron (hypoferremia), low hemoglobin or hematocrit levels, decreased red blood cell or reticulocyte numbers, increased soluble transferrin receptor, iron restricted erythropoiesis; symptoms include fatigue, pallor and poor exercise tolerance. The severity of indicators may be determined by subjective or objective measures which are known to those skilled in the art. As used herein, "treatment" or "therapy" means to administer a composition of antisense compounds, erythropoietin (or other ESA), or of antisense compounds combined with erythropoietin (or other ESA) to effect an alteration or improvement of the disease or condition; the antisense compounds being targeted to a nucleic acid encoding hepcidin. Prevention, amelioration, and/or treatment may require administration of multiple doses at regular intervals, or prior to exposure to an agent (e.g., a chemotherapeutic) to alter the course of the condition or disease. Moreover, a single agent may be used in a single individual for each prevention, amelioration, and treatment of a condition or disease sequentially or concurrently. Moreover, the compounds and compositions disclosed herein may be administered or delivered to a patient who is receiving a particular therapy, compound, agent or composition. In this case, the receiving can occur prior to the method of administering or delivering, or it may occur simultaneously or following the administration or delivery of the compound or composition. Additionally, regardless of when the receiving begins relative to administration or delivery, it may continue after the administration or delivery.

Disclosed herein are antisense compounds, including antisense oligonucleotides, for use in modulating the expression of nucleic acid molecules encoding hepcidin. This modulation is accomplished by providing antisense compounds that are designed to target and hybridize with one or more target nucleic acid molecules encoding hepcidin (SEQ ID NOS: 1, 2 or 3.). As used herein, the terms "target nucleic acid" and "nucleic acid molecule encoding hepcidin" have been used for convenience to encompass RNA (including pre-mRNA and mRNA or portions thereof) transcribed from DNA encoding hepcidin and also cDNA derived from such RNA. In a preferred embodiment, the target nucleic acid is an mRNA encoding hepcidin.

Target Nucleic Acids

"Targeting" refers to the design and selection of antisense compounds capable of hybridizing to or complementary to a particular target nucleic acid molecule. Antisense compounds selected by this process are said to be "targeted to" the target nucleic acid molecule. Targeting can be a multistep process that usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes hepcidin.

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Antisense compounds targeted to such variants are within the scope of the oligomeric compounds as described herein.

Target Names, Synonyms, Features

Accordingly, there are provided compositions and methods for modulating the expression of hepcidin. "Hepcidin" is also referred to as hepcidin antimicrobial peptide; HAMP; HAMP1; HEPC; HFE2; LEAP-1; LEAP1; and liver-expressed antimicrobial peptide. Herein the term "hepcidin" is used. Table 1 lists the GenBank accession numbers of sequences corresponding to nucleic acid molecules encoding hepcidin (nt=nucleotide), the date the version of the sequence was entered in GenBank, and the corresponding SEQ ID NO in the instant application, when assigned. Each sequence is incorporated herein by reference.

TABLE 1

Gene Targets

| Species | Genbank # | Genbank Date | SEQ ID NO |
|---|---|---|---|
| Human | BM719679.1 | Mar. 1, 2002 | 1 |
| Human | NM_021175.2 | Jul. 23, 2004 | 2 |
| Human | nucleotides 7819907 to 7825131 of NT_011196.11 | Jan, 5, 2003 | 3 |

TABLE 1-continued

Gene Targets

| Species | Genbank # | Genbank Date | SEQ ID NO |
|---|---|---|---|
| Mouse | NM_032541.1 | May 28, 2001 | 4 |
| Mouse | the complement of nucleotides 3978217 to 3980665 of NT_039413.1 | Feb. 24, 2003 | 5 |

Modulation of Target Expression

Modulation of expression of a target nucleic acid can be achieved through alteration of any number of nucleic acid functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of hepcidin. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of antisense compounds on target nucleic acid expression can be tested in any of a variety of cell types provided that the target nucleic acid is present at measurable levels. The effect of antisense compounds on target nucleic acid expression can be routinely determined using, for example, PCR, Northern blot analysis or measurement of hepcidin polypeptide in the urine or serum of an animal (e.g., ELISA or Western blots). Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells are prepared by methods known in the art.

Assaying Modulation of Expression

Modulation of hepcidin expression can be assayed in a variety of ways known in the art. Hepcidin mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant description.

Levels of a protein encoded by hepcidin can be quantitated in a variety of ways well known in the art, such as immunoprecipitation, Western blot analysis (immunoblotting), ELISA or fluorescence-activated cell sorting (FACS). Antibodies directed to a protein encoded by hepcidin can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997.

Active Target Segments

The locations on the target nucleic acid defined by having one or more active antisense compounds targeted thereto are referred to as "active target segments." When an active target segment is validated by multiple antisense compounds, the compounds are preferably separated by no more than about 30 nucleotides on the active target segment, more preferably no more than about 10 nucleotides on the target sequence, even more preferably the compounds are contiguous, and most preferably the compounds are overlapping. In a preferred embodiment, at least 50%, preferably at least 70% of the oligonucleotides targeted to the active target segment modulate expression of their target RNA at least 40%. There may be substantial variation in activity (e.g., as defined by percent reduction or activity ranking) of each antisense compounds within an active target segment. Active antisense compounds are those that modulate the expression of their target RNA. Active antisense compounds reduce expression of their target RNA at least 10%, preferably at least 20%. In other embodiments at least 50%, at least 55%, at least 60%, at least 65%, at least 70%, at least 75%, at least 80%, at least 85%, at least 90%, at least 95% or at least 99%. In a more preferred embodiment, the level of reduction required to define an active antisense compound is based on the results from the screen used to define the active target segments.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methylcytosine and the artificial base known as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Identity

Antisense compounds, or a portion thereof, may have a defined percent identity to a SEQ ID NO, or a compound having a specific CMPD number. As used herein, a sequence is identical to the sequence disclosed herein if it has the same nucleobase pairing ability. For example, an RNA which contains uracil in place of thymidine in the disclosed sequences would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the antisense compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the current disclosure. Non-identical versions are those wherein each base does not have the same pairing activity as the antisense compounds disclosed herein. In a preferred embodiment the antisense compounds can have about 3 mismatched base pairs. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or identical bases corresponding to the antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to another 20-mer is also 80% identical to that other 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. Herein, the complement of an active target segment may constitute a single portion. In a preferred embodiment, the oligomeric compounds are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA in an oocyte injection model. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to reduce translation, albeit at a more modest level than the 28 or 42 nucleobase ASOs.

Therapeutics

The antisense compounds disclosed herein can be used to modulate the expression of hepcidin in an animal, such as a human. In one non-limiting embodiment, the methods comprise the step of administering to said animal in need of therapy for a disease or condition associated with hepcidin an effective amount of an antisense compound that reduces expression of hepcidin. A disease or condition associated with hepcidin includes, but is not limited to, anemia. In one embodiment, the antisense compounds effectively reduce the levels or function of hepcidin RNA. Because reduction in hepcidin mRNA levels can lead to alteration in hepcidin protein products of expression as well, such resultant alterations can also be measured. Antisense compounds that effectively reduce the level or function of hepcidin RNA or protein products of expression are considered an active antisense compounds. In one embodiment, the antisense compounds reduce the expression of hepcidin causing a reduction of target RNA by at least about 10%, by at least about 20%, by at least about 25%, by at least about 30%, by at least about 40%, by at least about 50%, by at least about 60%, by at least about 70%, by at least about 75%, by at least about 80%, by at least about 85%, by at least about 90%, by at least about 95%, by at least about 98%, by at least about 99%, or by 100%.

For example, the reduction of the expression of hepcidin can be measured in a bodily fluid, tissue or organ of the animal. Methods of obtaining samples for analysis, such as body fluids (e.g., blood, serum or urine), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the hepcidin expression in the aforementioned fluids, tissues or organs, collected from an animal contacted with one or more oligomeric compounds targeted to a nucleic acid encoding hepcidin, by routine clinical methods known in the art. These biomarkers include but are not limited to:serum iron levels, hemoglobin levels, transferrin levels, iron restricted erythropoesis, liver transaminases, bilirubin, albumin, blood urea nitrogen, creatine and other markers of kidney and liver function; interleukins, tumor necrosis factors, chemokines, cytokines and other markers of anemia.

The antisense compounds can be utilized in pharmaceutical compositions by adding an effective amount of a compound to a suitable pharmaceutically acceptable diluent or carrier. Acceptable carriers and dilutents are well known to those skilled in the art. Selection of a dilutent or carrier is based on a number of factors, including, but not limited to, the solubility of the compound and the route of administration. Such considerations are well understood by those skilled in the art. In one aspect, the antisense compounds reduce the expression of hepcidin. The compounds can also be used in the manufacture of a medicament for the treatment of diseases and conditions related to hepcidin expression.

Methods whereby bodily fluids, organs or tissues are contacted with an effective amount of one or more of the antisense compounds or compositions are also contemplated. Bodily fluids, organs or tissues can be contacted with one or more of the antisense compounds resulting in modulation of hepcidin expression in the cells of bodily fluids, organs or tissues. An effective amount can be determined by monitoring the modulatory effect of the antisense compound or compounds or compositions on target nucleic acids or their products by methods routine to the skilled artisan.

Thus, provided herein is the use of an isolated single- or double-stranded antisense compound targeted to hepcidin in the manufacture of a medicament for the treatment of a disease or disorder by means of the method described above. In a preferred embodiment, the antisense compound is a single stranded antisense compound. Also provided herein is the use of a composition comprising erythropoietin or other ESA and an antisense compound targeted to hepcidin in the manufacture of a medicament for the treatment of a disease or disorder by the means of the method described above.

Kits, Research Reagents, and Diagnostics

The antisense compounds can be utilized for diagnostics, and as research reagents and kits. Furthermore, antisense compounds, which are able to reduce gene expression with specificity, are often used by those of ordinary skill to elucidate the function of particular genes or to distinguish between functions of various members of a biological pathway.

For use in kits and diagnostics, the antisense compounds, either alone or in combination with other compounds or therapeutics, for example ESAs, can be used as tools in differential and/or combinatorial analyses to elucidate expression patterns of a portion or the entire complement of genes expressed within cells and tissues. Methods of gene expression analysis are well known to those skilled in the art.

Compounds

The term "oligomeric compound" refers to a polymeric structure capable of hybridizing to a region of a nucleic acid molecule. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides.

An "antisense compound" or "antisense oligomeric compound" refers to an oligomeric compound that is at least partially complementary to the region of a target nucleic acid molecule to which it hybridizes and which modulates (increases or decreases) its expression. This term includes oligonucleotides, oligonucleosides, oligonucleotide analogs, oligonucleotide mimetics, antisense compounds, antisense oligomeric compounds, and chimeric combinations of these. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self complementarity to allow for hybridization and formation of a fully or partially double-stranded compound. The oligomeric compounds are not autocatalytic. As used herein, "auto-catalytic" means a compound has the ability to promote cleavage of the target RNA in the absence of accessory factors, e.g. proteins.

In one embodiment, the antisense compound comprises a single stranded oligonucleotide. In some embodiments the antisense compound contains chemical modifications. In a preferred embodiment, the antisense compound is a single stranded, chimeric oligonucleotide wherein the modifications of sugars, bases, and internucleoside linkages are independently selected.

The antisense compounds may comprise an antisense compound from about 12 to about 35 nucleobases (i.e. from about 12 to about 35 linked nucleosides). In other words, a single-stranded anisense compound comprises from about 12 to about 35 nucleobases, and a double-stranded antisense compound (such as a siRNA, for example) comprises two strands, each of which is independently from about 12 to about 35 nucleobases. This includes oligonucleotides 15 to 35 and 16 to 35 nucleobases in length. Contained within the antisense compounds (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases.

Antisense compounds about 12 to 35 nucleobases in length, preferably about 15 to 35 nucleobases in length, comprising a stretch of at least eight (8), preferably at least 12, more preferably at least 15 consecutive nucleobases selected from within the active target regions are considered to be suitable antisense compounds as well.

Modifications can be made to the antisense compounds and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxyethoxy (2'-MOE) sugar modifications, inverted abasic caps, deoxynucleobases, and bicyclic nucleic acids such as locked nucleic acids (LNA) and ethylene nucleic acid (ENA).

In one embodiment, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang.

Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligo-nucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the oligomeric compounds. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds may also contain one or more nucleosides having modified sugar moieties. The furanosyl sugar ring of a nucleoside can be modified in a number of ways including, but not limited to, addition of a substituent group bridging two non-geminal ring atoms to form a bicyclic nucleic acid (BNA) and substitution of an atom or group such as —S—, —N(R)— or —C(R$_1$)(R$_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH$_2$)$_2$—O-2' bridge); and substituted sugars, especially 2'-substituted sugars having a 2'-F, 2'-OCH$_2$ or a 2'-O(CH$_2$)$_2$—OCH$_3$ substituent group. Sugars can also be replaced with sugar mimetic groups among others. Methods for the preparations of modified sugars are well known to those skilled in the art.

Included herein are internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., (2000) Nuc Acid Res., 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

As used herein, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

Provided herein are compounds having reactive phosphorus groups useful for forming internucleoside linkages including for example phosphodiester and phosphorothioate internucleoside linkages. Methods of preparation and/or purification of precursors or antisense compounds are not a limitation of the compositions or methods described herein. Methods for synthesis and purification of DNA, RNA, and the antisense compounds are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of reduction of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used in herein the term "motif" refers to the orientation of modified sugar moieties and/or sugar mimetic groups in an antisense compound relative to like or differentially modified or unmodified nucleosides. As used herein, the terms "sugars", "sugar moieties" and "sugar mimetic groups' are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used herein the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings.

As used herein the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used herein the term "fully modified motif" refers to an antisense compound comprising a contiguous sequence of nucleosides wherein essentially each nucleoside is a sugar modified nucleoside having uniform modification.

As used herein the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used herein the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used herein the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), alpha or beta, or as (D) or (L) such as for amino acids et al. The present description of oligomeric compounds is meant to include all such possible isomers, as well as their racemic and optically pure forms.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The current description is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

Salts, Prodrugs and Bioequivalents

The antisense compounds comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., phosphodiester backbone linkages) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Combinations

Compositions can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions can contain two or more antisense compounds targeted to different regions of the same nucleic acid target. Compositions can also include other non-antisense compound therapeutic agents. For example, disclosed herein are combinations comprising an antisense oligonucleotide targeted to hepcidin combined with erythropoietin. Two or more combined compounds may be used together or sequentially. Likewise, one or more compound and one or more therapeutic agent may be used together or sequentially. For example, disclosed herein are compounds and therapeutics and methods of use wherein the compounds are administered simultaneously, or at distinct timepoints. For example, an antisense oligonucleotide targeted to a nucleic acid encoding hepcidin can be administered either simultaneously with or at a distinct timepoint from erythropoietin.

Nonlimiting Disclosure and Incorporation by Reference

While certain compounds, compositions and methods have been described with specificity in accordance with certain embodiments, the following examples serve only to illustrate the compounds and methods and are not intended to limit the same. Each of the references, GenBank accession numbers, and the like recited in the present application is incorporated herein by reference in its entirety.

EXAMPLE 1

Cell Types and Transfection Methods

The effect of oligomeric compounds on target nucleic acid expression was tested on the following cell types.

Mouse Primary Hepatocytes: Primary mouse hepatocytes were prepared from CD-1 mice purchased from Charles River Labs (Wilmington, Mass.). Primary mouse hepatocytes were routinely cultured in Hepatocyte Attachment Media supplemented with 10% fetal bovine serum, 1% penicillin/streptomycin (both from Sigma-Aldrich, St. Louis, Mo.), 1% antibiotic-antimitotic (Invitrogen Life Technologies, Carlsbad, Calif.) and 10 nM bovine insulin (Sigma-Aldrich, St. Louis, Mo.). Cells were seeded into 96-well plates (Falcon-Primaria #3872) coated with 0.1 mg/ml collagen at a density of approximately 10,000 cells/well for use in oligomeric compound transfection experiments.

HepG2: The human hepatocarcinoma cell line was obtained from the American Type Culture Collection (Manassas, Va.). HepG2 cells were routinely cultured in minimum essential medium (Eagle) with 2 mM L-glutamine and Earle's BSS (Cambrex, East Rutherford, N.J.) adjusted to contain 1.5 g/L sodium bicarbonate, 0.1 mM non-essential amino acids, and 1.0 mM sodium pyruvate, 90%; fetal bovine serum, 10% (sigma-Aldrich, St. Louis, Mo.) at a temperature of 37.degrees.C. Cells were routinely passaged by trypsinization and dilution when they reached approximately 80% confluence. Cells were seeded into 96-well plates (Falcon-Primaria #3872) at a density of approximately 5000 cells/well for use in oligomeric compound transfection experiments.

When cells reached 65-75% confluency, they were treated with oligonucleotide. Oligonucleotide was mixed with LIPOFECTIN™ invitrogen Life Technologies, Carlsbad, Calif.) in OPTI-MEM™-1 reduced serum medium (Invitrogen Life Technologies, Carlsbad, Calif.) to achieve the desired concentration of oligonucleotide and a LIPOFECTIN™ concentration of 2.5 or 3.micro.g/mL per 100 nM oligonucleotide. This transfection mixture was incubated at room temperature for approximately 0.5 hours. For cells grown in 96-well plates, wells were washed once with 100.micro.L OPTI-MEM™-1 and then treated with 130.micro.L of the transfection mixture. Cells were treated and data were obtained in duplicate or triplicate. After approximately 4-7 hours of treatment at 37.degrees.C, the medium containing the transfection mixture was replaced with fresh culture medium. Cells were harvested 16-24 hours after oligonucleotide treatment.

Control oligonucleotides were used to determine the optimal oligomeric compound concentration for a particular cell line. Furthermore, when oligomeric compounds were tested in oligomeric compound screening experiments or phenotypic assays, control oligonucleotides were tested in parallel.

The concentration of oligonucleotide used varied from cell line to cell line. To determine the optimal oligonucleotide concentration for a particular cell line, the cells were treated with a positive control oligonucleotide at a range of concentrations. The concentration of positive control oligonucleotide that resulted in about an 80% reduction of the target mRNA was then utilized as the screening concentration for new oligonucleotides in subsequent experiments for that cell line. If 80% reduction was not achieved, the lowest concentration of positive control oligonucleotide that resulted in a 60% reduction of the target mRNA was then utilized as the oligonucleotide screening concentration in subsequent experiments for that cell line. If 60% reduction was not achieved, that particular cell line was deemed as unsuitable for oligonucleotide transfection experiments.

EXAMPLE 2

Real-Time Quantitative PCR Analysis of Hepcidin mRNA Levels

Quantitation of hepcidin mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the hepcidin being measured were evaluated for their ability to be "multiplexed" with a GAPDH amplification reaction. After isolation the RNA was subjected to sequential reverse transcriptase (RT) reaction and real-time PCR, both of which were performed in the same well. RT and PCR reagents were obtained from Invitrogen Life Technologies (Carlsbad, Calif.). RT, real-time PCR was carried out in the same by adding 20.micro.L PCR cocktail (2.5×PCR buffer minus MgCl.sub.2, 6.6 mM MgCl.sub.2, 375.micro.M each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30.micro.L total RNA solution (20-200 ng). The RT reaction was carried out by incubation for 30 minutes at 48.degrees.C. Following a 10 minute incubation at 95.degrees.C to activate the PLATINUM® Taq, 40 cycles of a two-step PCR protocol were carried out: 95.degrees.C for 15 seconds (denaturation) followed by 60.degrees.C for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170.micro.L of RiboGreen™ working reagent (RiboGreen™ reagent diluted 1:350 in 10 mM Tris-HCl, 1 mM EDTA, pH 7.5) was pipetted into a 96-well plate containing 30.micro.L purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

| Hepcidin-specific primers and probes for use in real-time PCR | | | | |
|---|---|---|---|---|
| Species | Target SEQ ID NO | Sequence Description | Sequence (5' to 3') | SEQ ID NO |
| Human | 2 | Forward Primer | AGGAGGCGAGACACCCACTT | 6 |
| Human | 2 | Reverse Primer | TCCCACACTTTGATCGATGACA | 7 |
| Human | 2 | Probe | CATCTGCATTTTCTGCTGCGGCTG | 8 |
| Mouse | 4 | Forward Primer | TGCAGAAGAGAAGGAAGAGAGACA | 9 |
| Mouse | 4 | Reverse Primer | CACACTGGGAATTGTTACAGCATT | 10 |
| Mouse | 4 | Probe | CAACTTCCCCATCTGCATCTTCTGCTGT | 11 |

EXAMPLE 3

Antisense Reduction of Human Hepcidin Expression by Oligomeric Compounds

A series of antisense oligonucleotide compounds was designed to target different regions of human hepcidin RNA, using published sequences or portions of published sequences as cited in Table 1. The compounds are shown in Table 3. Methods for designing and testing antisense oligonucleotides for reduction of mRNA target expression are discussed herein and well known to those skilled in the art. Although an antisense oligonucleotide is reported in Table 3 as being targeted to a particular sequence, one ordinarily skilled in the art will know that these sequences may also target other sequences. For example, in Table 3 SEQ ID NO: 50 is reportedly designed to target nucleotides 261 to 280 of SEQ ID NO: 2. However, SEQ ID NO: 50 is also fully complementary to nucleotides 486 to 505 of SEQ ID NO: 1 and nucleotides 4662 to 4681 of SEQ ID NO: 3.

The compounds were analyzed for their effect on target mRNA levels by using quantitative real time RT-PCR as described above. The screen identified active target segments within these regions of the human hepcidin mRNA sequence and the genomic sequence encoding hepcidin mRNA, specifically GenBank numbers BM719679.1; NM_021175.2; and nucleotides 7819907 to 7825131 of NT_011196.11 (SEQ ID NOS: 1; 2; and 3, respectively). The activity of these antisense oligonucleotides to reduce hepcidin mRNA expression is ranked as follows: +++++ (reduction of target by greater than about 70%), ++++ (reduction of target by greater than about 70% to about 74%), +++ (reduction of target by greater than about 60% to about 69%), ++ (reduction of target by greater than about 55% to about 60%), + (reduction of target by greater than about 50% to about 55%) or bc (below cut-off or lesser than about 50%). Antisense compounds having an activity ranking of bc may have shown some reduction of hepcidin expression but fell below the cut-off level for this screening assay.

TABLE 3

Reduction of Human Hepcidin mRNA Levels by Antisense Oligonucleotides

| CMPD # | Target SEQ ID NO | Target Start Site | Activity Sequence (5' to 3') | Ranking | SEQ ID NO |
|---|---|---|---|---|---|
| 392287 | 1 | 32 | AATGCACAGGCCCTGCCATC | + | 12 |
| 392288 | 1 | 38 | CACAGAAATGCACAGGCCCT | bc | 13 |
| 392289 | 1 | 43 | TCAAGCACAGAAATGCACAG | bc | 14 |
| 392290 | 1 | 48 | CCCACTCAAGCACAGAAATG | bc | 15 |
| 392291 | 1 | 53 | CAAGGCCCACTCAAGCACAG | +++ | 16 |
| 392292 | 1 | 58 | ACTTTCAAGGCCCACTCAAG | ++++ | 17 |
| 392280 | 1 | 66 | GCTGAACCACTTTCAAGGCC | bc | 18 |
| 392281 | 1 | 71 | TGGTTGCTGAACCACTTTCA | bc | 19 |
| 392282 | 1 | 91 | GAGGAATGAACACTTCTTCC | bc | 20 |
| 392283 | 1 | 96 | TTGTCGAGGAATGAACACTT | ++ | 21 |
| 392284 | 1 | 101 | TGTTGTTGTCGAGGAATGAA | bc | 22 |
| 392285 | 1 | 123 | CCAAGTCACCAGAGCCCGGG | +++++ | 23 |
| 392286 | 1 | 128 | GTCAGCCAAGTCACCAGAGC | ++++ | 24 |
| 392304 | 1 | 133 | CCAGTGTCAGCCAAGTCACC | bc | 25 |
| 392305 | 1 | 138 | GCCATCCAGTGTCAGCCAAG | + | 26 |
| 392306 | 1 | 143 | CCAGGGCCATCCAGTGTCAG | +++ | 27 |
| 392307 | 1 | 148 | TCATTCCAGGGCCATCCAGT | ++++ | 28 |
| 392308 | 1 | 153 | CTTTTTCATTCCAGGGCCAT | ++ | 29 |
| 392309 | 1 | 179 | GGCCCTTGCACATTTTGCCT | + | 30 |
| 392293 | 1 | 186 | CCAGATGGGCCCTTGCACAT | ++++ | 31 |
| 392294 | 1 | 191 | TGGTTCCAGATGGGCCCTTG | bc | 32 |
| 392295 | 1 | 196 | GGCCTTGGTTCCAGATGGGC | +++ | 33 |
| 392296 | 1 | 215 | GTGACAGTCGCTTTTATGGG | bc | 34 |

TABLE 3-continued

Reduction of Human Hepcidin mRNA
Levels by Antisense Oligonucleotides

| CMPD # | Target SEQ ID NO | Target Start Site | Sequence (5' to 3') | Activity Ranking | SEQ ID NO |
|---|---|---|---|---|---|
| 392297 | 1 | 220 | ACCGAGTGACAGTCGCTTTT | bc | 35 |
| 392298 | 1 | 225 | CTGGGACCGAGTGACAGTCG | + | 36 |
| 392299 | 1 | 547 | CAGGGCAGGTAGGTTCTACG | +++ | 37 |
| 392316 | 2 | 3 | TGTCTGGGACCGAGTGACAG | bc | 38 |
| 392323 | 2 | 8 | TCTGGTGTCTGGGACCGAGT | + | 39 |
| 392318 | 2 | 70 | CTGGGAGCTCAGTGCCATCG | +++++ | 40 |
| 392319 | 2 | 75 | CAGATCTGGGAGCTCAGTGC | bc | 41 |
| 392300 | 2 | 127 | AGAGCCACTGGTCAGGCTGG | +++++ | 42 |
| 392320 | 2 | 132 | AAAACAGAGCCACTGGTCAG | bc | 43 |
| 392302 | 2 | 137 | GTGGGAAAACAGAGCCACTG | +++ | 44 |
| 392310 | 2 | 161 | GCTCTGCAAGTTGTCCCGTC | ++++ | 45 |
| 392311 | 2 | 166 | TTGCAGCTCTGCAAGTTGTC | bc | 46 |
| 392303 | 2 | 212 | GGAACATGGGCATCCAGCTG | bc | 47 |
| 392313 | 2 | 217 | CCTCTGGAACATGGGCATCC | +++ | 48 |
| 392314 | 2 | 242 | GGAAGTGGGTGTCTCGCCTC | +++++ | 49 |
| 392315 | 2 | 261 | CAGCAGAAAATGCAGATGGG | +++++ | 50 |
| 392326 | 2 | 268 | GCAGCCGCAGCAGAAAATGC | +++++ | 51 |
| 392327 | 2 | 273 | TGACAGCAGCCGCAGCAGAA | +++ | 52 |
| 392328 | 2 | 278 | ATCGATGACAGCAGCCGCAG | +++++ | 53 |
| 392330 | 2 | 287 | CACACTTTGATCGATGACAG | ++ | 54 |
| 392329 | 2 | 292 | CATCCCACACTTTGATCGAT | ++++ | 55 |
| 392321 | 2 | 297 | CAGCACATCCCACACTTTGA | ++ | 56 |
| 392322 | 2 | 302 | TCTTGCAGCACATCCCACAC | bc | 57 |
| 392301 | 2 | 382 | TTATTCCAAGACCTATGTTC | ++ | 58 |
| 392317 | 2 | 390 | CAGCCATTTTATTCCAAGAC | +++ | 59 |
| 392324 | 2 | 395 | AGAACCAGCCATTTTATTCC | bc | 60 |
| 392325 | 2 | 400 | ACAAAAGAACCAGCCATTTT | bc | 61 |
| 392340 | 3 | 2917 | CCTGACCAGGATGGAGAAAT | +++ | 62 |
| 392341 | 3 | 2924 | CAAATTCCCTGACCAGGATG | + | 63 |
| 392339 | 3 | 2929 | TTTAACAAATTCCCTGACCA | bc | 64 |
| 392338 | 3 | 2934 | CAGTCTTTAACAAATTCCCT | bc | 65 |
| 392344 | 3 | 2942 | GTTTTCATCAGTCTTTAACA | +++ | 66 |
| 392343 | 3 | 2963 | TAGACACAATTATTTATTCA | bc | 67 |
| 392342 | 3 | 2968 | TGTACTAGACACAATTATTT | ++ | 68 |
| 392332 | 3 | 2973 | TAGAATGTACTAGACACAAT | + | 69 |
| 392333 | 3 | 2982 | ATTCACGAATAGAATGTACT | +++ | 70 |

TABLE 3-continued

Reduction of Human Hepcidin mRNA Levels by Antisense Oligonucleotides

| CMPD # | Target SEQ ID NO | Target Start Site | Activity Sequence (5' to 3') | Ranking | SEQ ID NO |
|---|---|---|---|---|---|
| 392331 | 3 | 2987 | ATGAGATTCACGAATAGAAT | bc | 71 |
| 392337 | 3 | 3018 | ATGGGTCACGGTCACTCTAC | ++ | 72 |
| 392336 | 3 | 3023 | GGCGAATGGGTCACGGTCAC | +++ | 73 |
| 392335 | 3 | 3028 | TGTGTGGCGAATGGGTCACG | bc | 74 |
| 392334 | 3 | 3227 | CAGCCCCTTGACCATGCCTG | ++++ | 75 |
| 392357 | 3 | 3260 | TGTCACTTTCTCATGAAACA | +++ | 76 |
| 392356 | 3 | 3278 | TCCAAGACGAAGGTCAACTG | bc | 77 |
| 392355 | 3 | 3349 | TTGTTCAGCCTGACCCTGGG | +++++ | 78 |
| 392354 | 3 | 3375 | TTATCCCCAAGTCCCACCAT | bc | 79 |
| 392353 | 3 | 3383 | CCTCAGCCTTATCCCCAAGT | bc | 80 |
| 392352 | 3 | 3398 | TAGGGACTGCCCACCCCTCA | +++++ | 81 |
| 392348 | 3 | 3420 | CTGCATGGTTGCCCACAAGA | ++++ | 82 |
| 392347 | 3 | 3425 | AGTGTCTGCATGGTTGCCCA | +++++ | 83 |
| 392346 | 3 | 3430 | AAATCAGTGTCTGCATGGTT | +++++ | 84 |
| 392345 | 3 | 3435 | AGGAAAAATCAGTGTCTGCA | ++++ | 85 |
| 392351 | 3 | 3782 | TCCATTTTAAAAACCTACAG | bc | 86 |
| 392350 | 3 | 3803 | GCCAGTGAGATTGTGGTTTT | bc | 87 |
| 392349 | 3 | 3808 | ACATGGCCAGTGAGATTGTG | +++ | 88 |
| 392312 | 3 | 4516 | GGCATCCAGCTGGCCCTGGC | +++ | 89 |

Each active target segment was targeted by multiple, active antisense oligonucleotides. This current example includes identification of active target segments identified on SEQ ID NO: 1, which active target segments are referred to as Regions A-E. The active target segments include nucleotides 456 to 527 for Region A, nucleotides 123 to 252 for Region B, nucleotides 352 to 405 for Region C, nucleotides 429 to 566 for Region D, and nucleotides 295 to 566 for Region E. Each of the oligonucleotides tested within Region A reduced expression of human hepcidin at least 55% (activity ranking ++). Four-fifths of the oligonucleotides tested in this region reduced expression by at least 75% (activity ranking +++++). Moreover, in Region D more than four-fifths of the oligonucleotides tested reduced expression by at least 55% (activity ranking ++) and more than one-half reduced expression by at least 70% (activity ranking ++++). In Region E, three-fourths of the oligonucleotides tested reduced expression by at least 50% (activity ranking +) and nearly one-half reduced expression by at least 70% (activity ranking ++++). Other active target segments on SEQ ID NO: 1 include Region C where three-fourths of the oligonucleotides tested reduced expression by at least 60% (activity ranking +++), and Region B where two-thirds of the oligonucleotides tested reduce expression by at least 50% (activity ranking +).

Active target segments were also identified on SEQ ID NO: 2 and SEQ ID NO: 3. The active target segments of SEQ ID NO: 2 are referred to as Regions F and G. Region F includes nucleotides 231 to 302. All of the nucleotides tested in Region F reduce expression by at least 55% (activity ranking ++), and two-thirds reduce at least 70% (activity ranking ++++). Region G includes nucleotides 204 to 341. More than four-fifths of the nucleotides tested in Region G reduce expression by at least 55% (activity ranking ++) and more than one-half reduce expression by at least 70% (activity ranking ++++).

The active target segments of SEQ ID NO: 3 are referred to as Regions H-K. Region H includes nucleotides 3398 to 3454 and all of the oligonucleotides tested in this region reduce expression by at least 70% (activity ranking ++++). Region I includes nucleotides 3249 to 3454. In Region I, three-fourths of the oligonucleotides tested reduced expression by at least 70% (activity ranking ++++) and one-half reduce by at least 75% (activity ranking +++++). Region J includes nucleotides 4643 to 4703. All of the oligonucleotides tested in this region reduce expression by at least 60% (activity ranking +++) and four-fifths reduce expression by at least 75% (activity ranking +++++). Region K includes nucleotides 4643 to 4743 and at least one-half of the oligonucleotides tested in this region reduce expression by at least 70% (activity ranking ++++).

Thus, Applicant has discovered regions of the human hepcidin mRNA that are highly active in response to antisense reduction. Identification of these regions allows for the design of antisense oligonucleotides that will modulate the expression of hepcidin. Antisense oligonucleotides can be designed the active target segments with at least a + activity ranking, more preferably with at least a ++ activity ranking and most preferably with a +++ activity ranking. One skilled in the art will readily recognize that the percent reduction is referred to herein as a relative amount of reduction compared to other oligonucleotides tested against SEQ ID NOS: 1, 2 or 3. Assay to assay variations in conditions results in changes from the absolute data received, however, the general trends and relative reduction will be substantially the same.

EXAMPLE 4

Antisense Reduction of Mouse Hepcidin Expression by Oligomeric Compounds

A series of antisense compounds was designed to target different regions of mouse hepcidin RNA, using published sequences or portions of published sequences as cited in Table 1. The compounds are shown in Table 4. The screen identified active target segments within these regions of the human hepcidin mRNA sequence and the genomic sequence encoding hepcidin mRNA, specifically GenBank numbers NM_032541.1 and the complement of nucleotides 3978217 to 3980665 of NT_039413.1 (SEQ ID NOS: 4 and 5, respectively). The activity of these antisense oligonucleotides are ranked based on measured percent reduction of the target from this study. The activity of these antisense oligonucleotides to reduce hepcidin mRNA expression is ranked as follows: +++++ (reduction of target by greater than about 70%), ++++ (reduction of target by greater than about 70% to about 74%), +++ (reduction of target by greater than about 60% to about 69%), ++ (reduction of target by greater than about 55% to about 60%), + (reduction of target by greater than about 50% to about 55%) or bc (below cut-off or lesser than about 50%). Antisense compounds having an activity ranking of bc may have shown some reduction of hepcidin expression but fell below the cut-off level for this screening assay.

TABLE 4

Reduction of Mouse Hepcidin mRNA Levels by Antisense Oligonucleotides

| CMPD # | Target SEQ ID NO | Target Start Site | Sequence (5' to 3') | Activity Ranking | SEQ ID NO |
|---|---|---|---|---|---|
| 326810 | 4 | 1 | TGCTGTGCAGTCTAAGGACT | +++ | 90 |
| 326811 | 4 | 6 | TGTTCTGCTGTGCAGTCTAA | bc | 91 |
| 326812 | 4 | 10 | CTTCTGTTCTGCTGTGCAGT | ++ | 92 |
| 326813 | 4 | 15 | CATGCCTTCTGTTCTGCTGT | ++++ | 93 |
| 326814 | 4 | 17 | ATCATGCCTTCTGTTCTGCT | +++ | 94 |
| 326815 | 4 | 22 | GTGCCATCATGCCTTCTGTT | +++++ | 95 |
| 326816 | 4 | 24 | GAGTGCCATCATGCCTTCTG | ++++ | 96 |
| 326817 | 4 | 27 | GCTGAGTGCCATCATGCCTT | +++++ | 97 |
| 326818 | 4 | 29 | GTGCTGAGTGCCATCATGCC | +++ | 98 |
| 326819 | 4 | 32 | CGAGTGCTGAGTGCCATCAT | bc | 99 |
| 326820 | 4 | 37 | GGGTCCGAGTGCTGAGTGCC | +++ | 100 |
| 326821 | 4 | 41 | GCCTGGGTCCGAGTGCTGAG | +++ | 101 |
| 326822 | 4 | 45 | GGCAGCCTGGGTCCGAGTGC | +++++ | 102 |
| 326823 | 4 | 50 | AGACAGGCAGCCTGGGTCCG | bc | 103 |
| 326824 | 4 | 55 | GCAGGAGACAGGCAGCCTGG | +++++ | 104 |
| 326825 | 4 | 71 | CTGGCAAGGAGGAGAAGCAG | bc | 105 |
| 326826 | 4 | 80 | CTGCTCAGGCTGGCAAGGAG | bc | 106 |
| 326827 | 4 | 84 | GGTGCTGCTCAGGCTGGCAA | bc | 107 |
| 326828 | 4 | 86 | GTGGTGCTGCTCAGGCTGGC | bc | 108 |
| 326829 | 4 | 88 | AGGTGGTGCTGCTCAGGCTG | ++++ | 109 |
| 326830 | 4 | 89 | TAGGTGGTGCTGCTCAGGCT | +++ | 110 |
| 326831 | 4 | 90 | ATAGGTGGTGCTGCTCAGGC | + | 111 |
| 326832 | 4 | 91 | GATAGGTGGTGCTGCTCAGG | bc | 112 |

TABLE 4-continued

Reduction of Mouse Hepcidin mRNA
Levels by Antisense Oligonucleotides

| CMPD # | Target SEQ ID NO | Target Start Site | Sequence (5' to 3') | Activity Ranking | SEQ ID NO |
|---|---|---|---|---|---|
| 326833 | 4 | 98 | TGATGGAGATAGGTGGTGCT | bc | 113 |
| 326834 | 4 | 99 | TTGATGGAGATAGGTGGTGC | bc | 114 |
| 326835 | 4 | 104 | ATCTGTTGATGGAGATAGGT | bc | 115 |
| 326836 | 4 | 105 | CATCTGTTGATGGAGATAGG | bc | 116 |
| 326837 | 4 | 112 | TCTGTCTCATCTGTTGATGG | bc | 117 |
| 326838 | 4 | 115 | TAGTCTGTCTCATCTGTTGA | bc | 118 |
| 326839 | 4 | 116 | GTAGTCTGTCTCATCTGTTG | bc | 119 |
| 326840 | 4 | 121 | GCTCTGTAGTCTGTCTCATC | + | 120 |
| 326841 | 4 | 124 | GCAGCTCTGTAGTCTGTCTC | +++++ | 121 |
| 326842 | 4 | 127 | GCTGCAGCTCTGTAGTCTGT | bc | 122 |
| 326843 | 4 | 130 | AAGGCTGCAGCTCTGTAGTC | +++ | 123 |
| 326844 | 4 | 135 | GTGCAAAGGCTGCAGCTCTG | +++ | 124 |
| 326845 | 4 | 141 | TTCCCCGTGCAAAGGCTGCA | bc | 125 |
| 326846 | 4 | 145 | TTTCTTCCCCGTGCAAAGGC | ++ | 126 |
| 326847 | 4 | 148 | TGCTTTCTTCCCCGTGCAAA | bc | 127 |
| 326848 | 4 | 158 | ATGTCTGCCCTGCTTTCTTC | bc | 128 |
| 326849 | 4 | 172 | GCATTGGTATCGCAATGTCT | + | 129 |
| 326850 | 4 | 176 | TTCTGCATTGGTATCGCAAT | bc | 130 |
| 326851 | 4 | 180 | TCTCTTCTGCATTGGTATCG | bc | 131 |
| 326852 | 4 | 200 | AAGTTGGTGTCTCTCTTCCT | ++ | 132 |
| 326853 | 4 | 203 | GGGAAGTTGGTGTCTCTCTT | +++++ | 133 |
| 326854 | 4 | 225 | TTTACAGCAGAAGATGGAGA | bc | 134 |
| 326855 | 4 | 229 | AGCATTTACAGCAGAAGATG | ++ | 135 |
| 326856 | 4 | 231 | ACAGCATTTACAGCAGAAGA | + | 136 |
| 326857 | 4 | 233 | TTACAGCATTTACAGCAGAA | +++ | 137 |
| 326858 | 4 | 238 | AATTGTTACAGCATTTACAG | bc | 138 |
| 326859 | 4 | 242 | TGGGAATTGTTACAGCATTT | bc | 139 |
| 326860 | 4 | 245 | CACTGGGAATTGTTACAGCA | bc | 140 |
| 326861 | 4 | 252 | GATACCACACTGGGAATTGT | bc | 141 |
| 326862 | 4 | 256 | AACAGATACCACACTGGGAA | bc | 142 |
| 326863 | 4 | 258 | GCAACAGATACCACACTGGG | +++++ | 143 |
| 326864 | 4 | 261 | TTTGCAACAGATACCACACT | +++ | 144 |
| 326865 | 4 | 263 | GTTTTGCAACAGATACCACA | + | 145 |
| 326866 | 4 | 266 | TATGTTTTGCAACAGATACC | bc | 146 |
| 326867 | 4 | 275 | GCTCTAGGCTATGTTTTGCA | +++++ | 147 |
| 326868 | 4 | 287 | GGTCAGGATGTGGCTCTAGG | +++++ | 148 |

TABLE 4-continued

Reduction of Mouse Hepcidin mRNA Levels by Antisense Oligonucleotides

| CMPD # | Target SEQ ID NO | Target Start Site | Sequence (5' to 3') | Activity Ranking | SEQ ID NO |
|---|---|---|---|---|---|
| 326869 | 4 | 291 | GAGAGGTCAGGATGTGGCTC | ++++ | 149 |
| 326870 | 4 | 293 | TAGAGAGGTCAGGATGTGGC | ++++ | 150 |
| 326871 | 4 | 296 | GTGTAGAGAGGTCAGGATGT | +++++ | 151 |
| 326872 | 4 | 334 | AGGGCAGGAATAAATAATGG | bc | 152 |
| 326873 | 4 | 336 | GGAGGGCAGGAATAAATAAT | bc | 153 |
| 326874 | 4 | 355 | ATTTCAAGGTCATTGGTGGG | bc | 154 |
| 326875 | 4 | 357 | TTATTTCAAGGTCATTGGTG | +++ | 155 |
| 326876 | 4 | 362 | CGTCTTTATTTCAAGGTCAT | +++++ | 156 |
| 326877 | 4 | 367 | AAAATCGTCTTTATTTCAAG | bc | 157 |
| 326878 | 4 | 369 | ATAAAATCGTCTTTATTTCA | bc | 158 |
| 326879 | 4 | 371 | AAATAAAATCGTCTTTATTT | bc | 159 |
| 326880 | 5 | 512 | GGGTGCTCACCTGTTGATGG | bc | 160 |
| 326881 | 5 | 1239 | TGCTTACTGCTGACTGCCAT | + | 161 |
| 326882 | 5 | 1244 | ATGCATGCTTACTGCTGACT | + | 162 |
| 326883 | 5 | 1259 | GCCTATGTGTATCATATGCA | ++ | 163 |
| 326884 | 5 | 1347 | CAGCAGAACCTCTACAGCCC | bc | 164 |
| 326885 | 5 | 1686 | TCTGTCTCATCTGTGAAAGC | bc | 165 |
| 326886 | 5 | 1746 | ATGCTCTTACCGCAATGTCT | bc | 166 |
| 326887 | 5 | 1829 | GCATTGGTATCTGTGTAAAG | + | 167 |

Each active target segment was targeted by multiple, active antisense oligonucleotides. This current example includes identification of active target segments identified on SEQ ID NO: 4, which active target segments are referred to as Regions L-O. The active target segments include nucleotides 287 to 315 for Region L, nucleotides 258 to 315 for Region M, nucleotides 1 to 74 for Region N, and nucleotides 80 to 199 for Region O. Each of the oligonucleotides tested within Region L reduced expression by at least 70% (++++) and three-fourths of them by at least 75% (+++++). Two-thirds of the oligonucleotides tested within Region M reduced expression by at least 70% (++++). About one-half of the oligonucleotides tested in Region N reduced expression by at least 70% (++++). This screen also identified regions with low activity when targeted with an antisense oligonucleotide. In Region O more than two-thirds of the oligonucleotides tested reduced expression by less than 50% (bc) and more than three-fifths by less than 35% (bc).

The active target segments for SEQ ID NO: 5 are referred to as Regions P-R. Region P includes nucleotides 1942 to 1972 and all of the oligonucleotides tested in this region reduce expression by at least 70% (+++). Region Q includes nucleotides 1991 to 2047 and three-fourths of the oligonucleotides tested in this region reduced expression by less than 50% (bc), and thus is considered a low-activity region. Similarly, for Region R, which includes nucleotides 474 to 531, more than two-thirds of the oligonucleotides tested in this region reduce expression by less than 50% (bc).

Thus, Applicant has discovered regions of the hepcidin mRNA that are highly responsive to antisense reduction and regions of the hepcidin mRNA that are less responsive to antisense reduction. Identification of these regions allows for the design of antisense oligonucleotides that will modulate the expression of hepcidin. One skilled in the art will readily recognize that the percent reduction is referred to herein as a relative amount of reduction compared to other oligonucleotides tested against SEQ ID NOS: 4 or 5. Assay to assay variations in conditions will results in changes from the absolute data received, however, the general trends and relative reduction will be substantially the same.

EXAMPLE 5

Antisense Oligonucleotides from about 12 to about 35 Nucleobases

As stated above, antisense oligonucleotides directed to a target or more preferably to an active target segment can be from about 12 to about 35 linked nucleobases. The following Table 5a provides a non-limiting example of such antisense oligonucleotides targeting SEQ ID NO 4.

TABLE 5a

Antisense Oligonucleotides from about
12 to about 35 Nucleobases

| Sequence | Length | |
|---|---|---|
| GGTCAGGATGTGGCTCTAGG | 20 nucleobases | (SEQ ID NO: 148) |
| GGTCAGGATGTGGCT | 15 nucleobases | (SEQ ID NO: 170) |
| CAGGATGTGGCTCTA | 15 nucleobases | (SEQ ID NO: 171) |
| GTCAGGATGTGG | 12 nucleobases | (SEQ ID NO: 172) |
| GAGAGGTCAGGATGTGGCTCTAGGCTATGTTTTGCA | 35 nucleobases | (SEQ ID NO: 173) |
| GTCAGGATGTGGCTCTAGGCTATGTTTT | 27 nucleobases | (SEQ ID NO: 174) |
| TGTGGCTCTAGGCTATGTTTGC | 22 nucleobases | (SEQ ID NO: 175) |

Antisense oligonucleotides directed to a target or more preferably to an active target segment can also contain mismatched nucleobases when compared to the target sequence. The following Table 5b provides a non-limiting example of such antisense oligonucleotides targeting nucleobases 287 to 306 of SEQ ID NO 4. Mismatched nucleobases are underlined.

TABLE 5b

Antisense Oligonucleotides from about 1-3
Nucleobases Mismatched to the Target Sequence

| Sequence | Number of mismatches to SEQ ID NO: 4 |
|---|---|
| GGTCAGGATGTGGCTCTAGG (SEQ ID NO: 148) | None |
| GGTCAGGATGTGGCTCAAGG (SEQ ID NO: 176) | One mismatch |
| GGTCAGGAAGTGGCTCTAGG (SEQ ID NO: 177) | One mismatch |
| GGTCAGTTTGTGGCTCTAGG (SEQ ID NO: 178) | Two mismatches |
| GGTGAGGATGTGGCTCCAGG (SEQ ID NO: 179) | Two mismatches |
| GGTCTGGATGTGCCTCTCGG (SEQ ID NO: 180) | Three mismatches |

EXAMPLE 6

Effects of Antisense Oligonucleotides Targeted to Mouse Hepcidin mRNA: In Vivo Evaluation in Normal Mice C57/Bl/6 mice were divided into treatment groups for injection with one of the following: antisense oligonucleotides targeting hepcidin mRNA (SEQ ID NOS: 4 and 5) at 50 mg/kg; antisense oligonucleotides that do not target hepcidin mRNA at 50 mg/kg; or saline. The animals received an initial dose and then were dosed twice per week for two weeks (5 doses total). The antisense oligonucleotides used in the study were all chimeric oligonucleotides ("gapmers") 20 nucleobases in length, composed of a central "gap" region consisting of 10 2'-deoxynucleotides, flanked on both the 5' and 3' ends by 5-nucleotide "wings." The wings are composed of 2'-methoxyethoxy nucleotides (2'-MOE). The internucleoside linkages are phosphorothioate (P=S) throughout the oligonucleotide. All cytidine residues are 5-methylcytidines. The sequences of the oligonucleotide are presented in Table 6.

TABLE 6

Antisense oligonucleotides used in
normal mouse in vivo screen assay

| Sequence | SEQ ID NO: |
|---|---|
| Targeted to hepcidin mRNA | |
| GGTCAGGATGTGGCTCTAGG | 148 |
| CGTCTTTATTTCAAGGTCAT | 156 |
| GTGCCATCATGCCTTCTGTT | 95 |
| Not targeted to hepcidin mRNA | |
| CCTTCCCTGAAGGTTCCTCC | 168 |
| GCTCATAGAACTGTCAGGCT | 169 |

At the end of the treatment period animals were sacrificed and tissues were harvested for assessment of levels of hepcidin mRNA in the liver, levels of hepcidin polypeptide in the liver and organ weight (specifically spleen and liver. Over the course of the study, data collected to evaluate overt toxicity, changes in body weight, changes in organ weight (specifically spleen and liver), changes in food intake, blood levels of aspartate aminotransferase (AST) and blood levels of alanine aminotransferase (ALT). There were no signs of overt toxicity or in changes to organ or body weight. There was an increase in levels of AST and ALT in the mice receiving one of the antisense oligonucleotides (SEQ ID NO: 95); however, levels for the other hepcidin targeting antisense oligonucleotides remained comperable to the saline control. Liver hepcidin levels were reduced by 60-70 percent for the hepcidin targeting antisense oligonucleotides compared to controls. A similar reduction was observed for liver hepcidin polypeptides. Hepcidin polypeptide levels were determined by Western blot of whole-liver lysates. Briefly, 50.micro.g of whole-liver lysate was electrophoresed on a 16% TG-gel. Hepcidin was detected with hepcidin antibody (Alpha Diagnostics, HEPC11-A, 0.3.micro.g/ml). FIG. 1. Thus, antisense oligonucleotides targeting hepcidin mRNA can result in a significant reduction in the levels of that mRNA and in turn the expression thereof.

EXAMPLE 7

Dose-Response of Antisense Oligonucleotide Targeting Hepcidin mRNA in Normal Mice C57/Bl/6 mice were dosed with 10, 25, 50 or 75 mg/kg of antisense oligonucleotide targeting hepcidin mRNA (SEQ ID NO: 145). C57/Bl 6 control mice received either saline or 10, 25, 50 or 75 mg/kg of an antisense oligonucleotide not targeted to hepcidin mRNA (SEQ ID NO: 168) The groups were given an initial dose and then were dosed twice per week for 2 weeks. Liver hepcidin mRNA and serum iron levels were measured at the end of the study. All antisense oligonucleotides used in this example were chimeric oligonucleotides ("gapmers") 20 nucleobases in length, composed of a central "gap" region consisting of 10 2'-deoxynucleotides, flanked on both the 5' and 3' ends by 5-nucleotide "wings." The wings are composed of 2'-methoxyethoxy nucleotides (2'-MOE). The internucleoside linkages are phosphorothioate (P=S) throughout the oligonucleotide. All cytidine residues are 5-methylcytidines.

Figure 2:
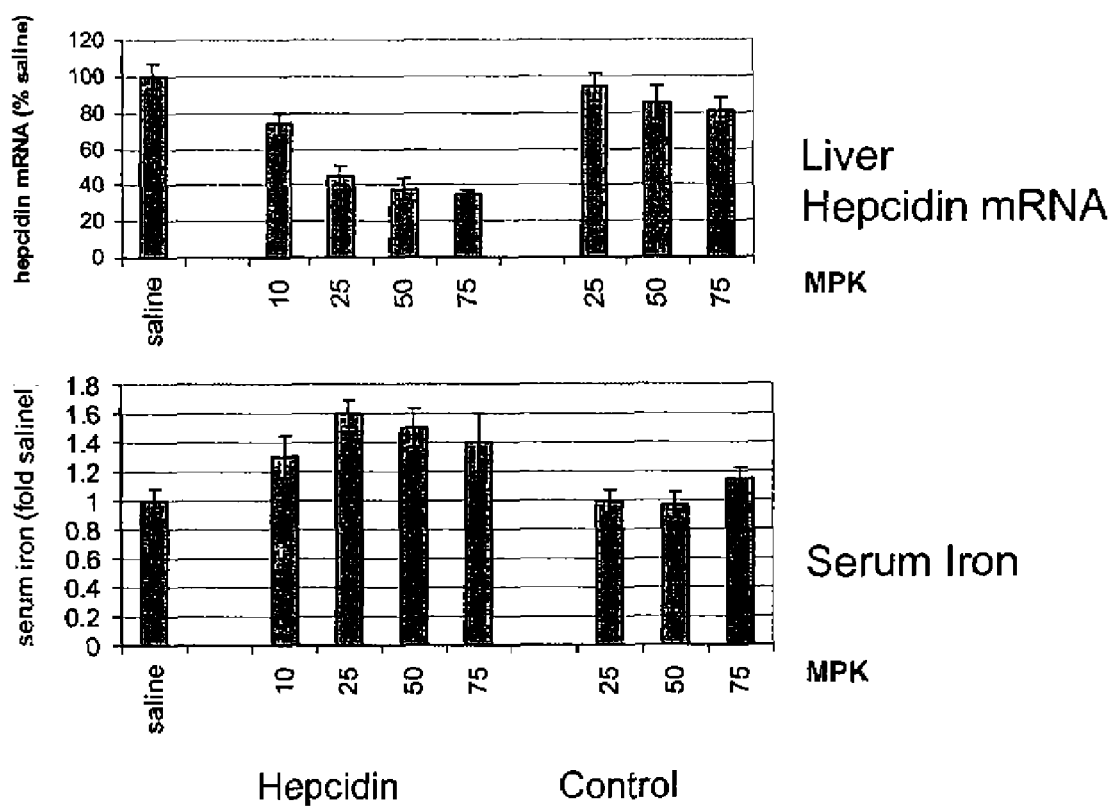
FIG. 2. Graph illustrating that delivery of 10-75 mg/kg of antisense oligonucleotide targeting hepcidin mRNA reduces hepcidin expression and in turn leads to an increase in serum iron levels in normal mice.

There was a reduction in liver hepcidin mRNA for the group receiving the antisense oligonucleotide targeting hepcidin as compared to saline control. A reduction was not observed for the control antisense oligonucleotide group as shown in FIG. 2. Also observed was a corresponding increase in serum iron levels for the treatment groups compared to saline. This same increase was not seen in the control oligonucleotide group. These data demonstrate that antisense oligonucleotides targeting hepcidin mRNA will cause a decrease in liver hepcidin mRNA and a corresponding increase in serum iron levels.

EXAMPLE 8

Effects of Antisense Reduction of Hepcidin in Normal and LPS Stimulated Mice: Dose-Response An ACD mouse model was prepared prior to treatment by injecting C57Bl/6 mice (Charles River Labs, Wilmington, Mass.) with lipopolysaccharide (LPS, Sigma-Aldrich, St. Louis, Mo.) for 6 hours (0.1 to 1 mg/kg intraperitoneal injection). (See, e.g. Ganz (2003) Blood, 102(3):783-785, and references therein). Injection of LPS caused an increase in cytokine production in these mice, which in turn resulted in a three fold increase in hepcidin production and an 80% reduction in serum iron levels.

A normal unstimulated mouse population and an LPS stimulated mouse population were each separated into treatment groups, antisense control groups and saline control groups. Mice in the LPS stimulated population were prepared using a 1 mg/kg intraperitoneal LPS injection for 6 hours. The treatment groups were treated with an antisense oligonucleotide targeted to mouse hepcidin mRNA (SEQ ID NOS: 4 and 5). The antisense control groups were treated with antisense oligonucleotide not targeted to mouse hepcidin. The saline control groups were injected with saline alone. The antisense oligonucleotide targeted to mouse hepcidin mRNA was (SEQ ID NO: 145). The control antisense oligonucleotide was SEQ ID NO 168. All mice were dosed at time point zero and then twice a week for two weeks using either 10, 25, 50 or 75 mg/kg of antisense oligonucleotide; 50 mg/kg of control oligonucleotide or using saline. All antisense oligonucleotides used in this example were chimeric oligonucleotides ("gapmers") 20 nucleobases in length, composed of a central "gap" region consisting of 10 2'-deoxynucleotides, flanked on both the 5' and 3' ends by 5-nucleotide "wings." The wings are composed of 2'-methoxyethoxy nucleotides (2'-MOE). The internucleoside linkages are phosphorothioate (P=S) throughout the oligonucleotide. All cytidine residues are 5-methylcytidines.

Figure 3:
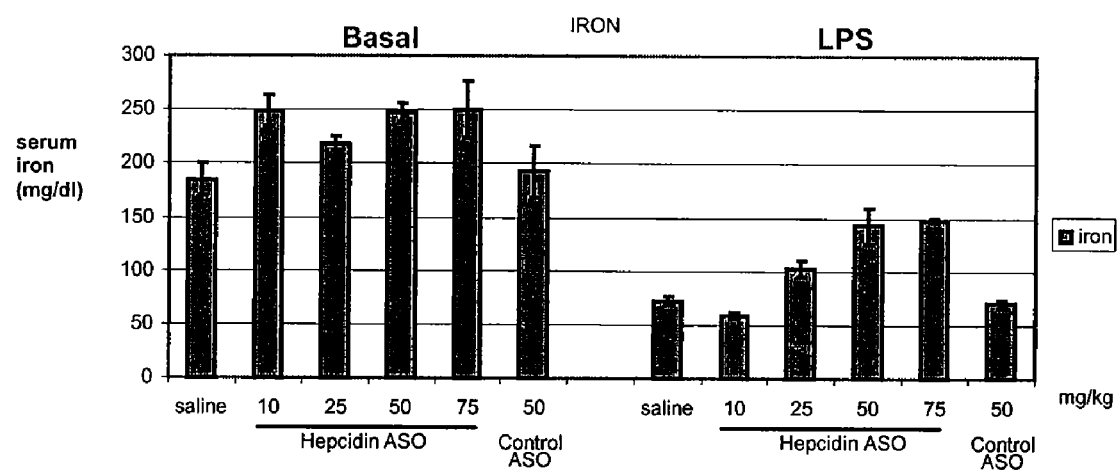
FIG. 3. Graph illustrating that antisense oligonucleotide reduction of hepcidin increases serum iron levels in both basal and LPS states in mice (N=4, SEM).
Figure 4A:
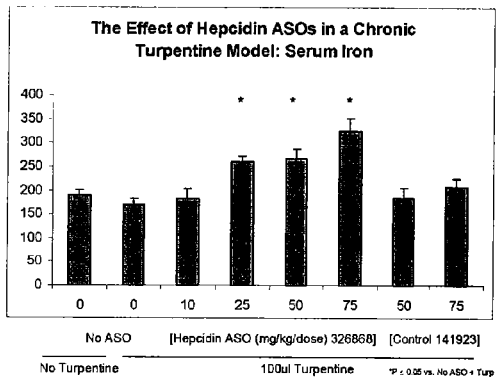
FIGS. 4a-d. Graphs illustrating responses to treatment with a compound that reduces the expression of mRNA encoding hepcidin for a number of clinical endpoints for anemia: a) serum levels; b) red blood cell count; c) hemoglobin levels; and d) hematocrit levels.
Figure 4B:
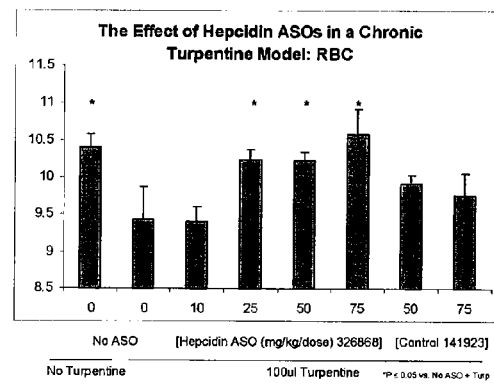
Figure 4C:
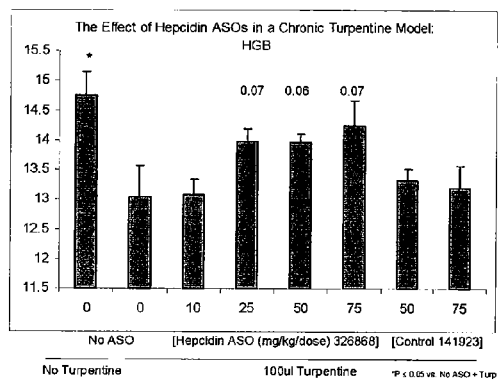
Figure 4D:
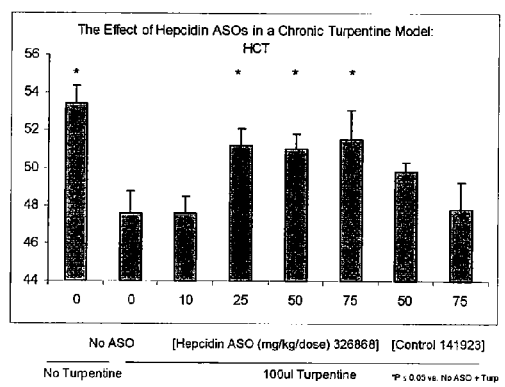

In both the normal mice and the LPS stimulated mice there was a reduction in levels of liver hepcidin mRNA for the 25, 50 and 75 mg/kg doses as compared to saline control. This same reduction was not seen in the antisense oligonucleotide control group. Additionally, there was a corresponding increase in serum iron levels for both the normal and LPS stimulated groups receiving antisense oligonucleotide targeting hepcidin as compared to saline. This same increase was not seen in the antisense oligonucleotide control group. This study shows that hepcidin increases serum iron levels in both normal and LPS stimulated mice. FIG. 3. Antisense oligonucleotides targeting hepcidin mRNA will reduce the levels of hepcidin mRNA in the liver, correlating with an increase in serum iron levels. This effect of the antisense oligonucleotide is observed in normal and LPS stimulated mice (ACD models). Thus, the antisense oligonucleotides are useful for treating subjects having low serum iron levels and disorders associated therewith.

EXAMPLE 9

Effects of Antisense Reduction of Hepcidin in Normal and Chronic Anemia Mice: Turpentine Mouse Model The effect of antisense compound treatment on acute and chronic anemia was determined using a turpentine induced anemia mouse model. Male C57Bl/6 mice (Charles River Laboratories, Wilmington, Mass.) weighing approximately 25 g were separated into one of a control group, an oligonucleotide control group or a treatment group. The control group mice received either no treatment (n=5) or treatment with 100 microliters turpentine only (n=5). The oligonucleotide control group mice received 100 microliters turpentine and a dosing regimen comprising either 50 mg/kg/dose of control compound (n=5) or 75 mg/kg/dose of control compound (n=5). The control compound was an antisense compound that is not targeted to a nucleic acid encoding hepcidin (CCTTCCCTGAAGGTTCCTCC, SEQ ID NO: 168). The treatment group mice received 100 microliters of turpentine and a dosing regimen comprising either 10 mg/kg/dose of treatment compound (n=5), 25 mg/kg/dose of treatment compound (n=5), 50 mg/kg/dose of treatment compound (n=5), or 75 mg/kg/dose of treatment compound (n=4). The treatment oligonucleotide is Cmpd 326868 (SEQ ID NO: 148). The turpentine injection stimulates an inflammatory response in the mice, and subsequently produces anemia. Turpentine mouse models of anemia are discussed in the literature. (Liuzzi, J P, Lichten, L A, Rivera, S, Blanchard, R K, Aydemir, T B, Knutson, M D, Ganz, T, and Cousins, R J, *PNAS*, v.102, n. 19, 6843-6848 (2005); Venihaki, M, Dikkes, P, Carrigan, A, and Karalis, K P, *J. Clin. Invest.*, 108:1159-1166 (2001)).

Mice in all groups were placed on a no-iron diet for two weeks, followed by a low-iron diet. At the same time the low-iron diet was started, the mice were subjected to the appropriate dosing regimen as described above. Briefly, the control group received no oligonucleotide, the oligonucleotide control group received 50 or 75 mg/kg/dose of SEQ ID NO: 168 twice a week for two weeks, and the treatment group received 10, 25, 50 or 75 mg/kg/dose of SEQ ID NO: 148 twice a week for two weeks. After two weeks of the dosing regimen, all mice in the oligonucleotide group and in the treatment group received an injection comprising 100 microliters of turpentine (Sigma-Aldrich, St. Louis, Mo.). In the control group, only half of the mice population received an injection comprising 100 microliters of turpentine and the other half of the population received a saline injection only. The injections were delivered subcutaneously to the left hind limb of each mouse. To obtain acute anemia endpoints, blood was drawn at 16 hours post turpentide injection. For chronic anemia endpoints, the dosing regimen described above continued for another two weeks after turpentine injection. Blood was drawn at two weeks post-turpentine injection and at 24 hours after the final oligonucleotide injection was delivered. Mice were then sacrificed.

Analysis of the serum iron from acute blood draw showed that the turpentine injection produced a significant reduction in the serum iron levels at 16 hours post turpentine injection. The serum iron level reduction was reversed in a dose responsive manner for the treatment group. At two weeks post injection there was a dose dependent improvement in the clinical endpoints of anemia compared to the control group and the oligonucleotide control group. Table 7 and FIGS. 4a-d shows the dose dependent improvement in serum iron levels, red blood cell count, hematocrit levels and hemoglobin levels.

ries, Wilmington, Mass.) weighing approximately 25 g were fed a "no iron" diet (2.7 ppm iron) for 2 weeks and subsequently switched to a "low iron" diet (47 ppm iron) for the remainder of the study. Upon switch to the low iron diet, two weeks prior to sacrifice, mice were treated via subcutaneous injection with saline (vehicle) or a single 100.micro. L dose of turpentine. Hepcidin antisense oligonucleotide (CMPD # 326868, 50 mg/kg, which is SEQ ID NO: 148) was administered via subcutaneous injection to the appropriate groups of animals (as indicated in FIGS. 5a-5c), two times per week, beginning 24 hours following turpentine treatment. EPO was administered daily, for the last four days of the study, by intraperitoneal injection to indicated animals at indicated doses (0-25 units/day). Thus, in this study, in indicated mice, regular treatment with antisense oligonucleotide targeted to hepcidin began prior to regular treatment with erythropoietin. After the first administration, each treatment was continued at regular intervals for the remainder of the study. At the end of the treatment period, animals were sacrificed and tissues and blood taken for assessment of levels hepcidin mRNA and phenotypic endpoints. Results from this study showed that hepcidin ASO in combination with EPO was well tolerated.

TABLE 7

The Effect of Hepcidin ASO in a Chronic Turpentine Model: Serum Iron, Red Blood Cell (RBC) Count, Hemoglobin Levels and Hematocrit Levels

| Turpentine | Control Group - | | Oligonucleotide Control Group | | Treatment Group | | | |
|---|---|---|---|---|---|---|---|---|
| (.micro.l) | 0 | 100 | 100 | 100 | 100 | 100 | 100 | 100 |
| CMPD | none | none | 50 mg/kg 141923 | 75 mg/kg 141923 | 10 mg/kg 326868 | 25 mg/kg 326868 | 50 mg/kg 326868 | 75 mg/kg 326868 |
| Serum Iron | | | | | | | | |
| (.micro.g/dL) | 190.6 | 170.6 | 186.0 | 208.2 | 182.8 | 260.8 | 266.6 | 325.5 |
| (SD) | (±24.1) | (±28.1) | (±44.4) | (±40.0) | (±44.3) | (±22.9) | (±46.0) | (±55.7) |
| RBC | | | | | | | | |
| ($10^6$/.micro.l) | 10.4 | 9.4 | 9.9 | 9.8 | 9.4 | 10.2 | 10.2 | 10.6 |
| (SD) | (±0.4) | (±1.0) | (±0.2) | (±0.7) | (±0.5) | (±0.3) | (±0.3) | (±0.8) |
| Hemoglobin | | | | | | | | |
| (g/dL) | 14.8 | 13.0 | 13.3 | 13.2 | 13.1 | 14.0 | 14.0 | 14.3 |
| (SD) | (±0.8) | (±1.2) | (±0.4) | (±0.8) | (±0.6) | (±0.5) | (±0.3) | (±0.9) |
| Hematocrit | | | | | | | | |
| (%) | 53.4 | 47.6 | 49.8 | 47.8 | 47.6 | 51.2 | 51.0 | 51.5 |
| (SD) | (±2.1) | (±2.6) | (±1.1) | (±3.3) | (±1.9) | (±1.9) | (±1.7) | (±3.5) |

The turpentine mouse model of anemia provides data for endpoints of chronic anemia, such as RBC count, hemoglobin levels and hematocrit levels, as well as serum iron levels. Treating these anemic mice with an antisense compound that targets and inhibits expression of nucleic acids encoding hepcidin polypeptide results in a dose dependent improvement in these endpoints.

EXAMPLE 10

Effects of Antisense Reduction of Hepcidin in Chronic Anemia (Turpentine Mouse Model) Treated with Erythropoietin The effect of antisense compound treatment on chronic anemia, in combination with erythropoietin (EPO) treatment was determined using the chronic turpentine induced anemia mouse model. Male C57Bl/6 mice (Charles River Labora- Hepcidin mRNA levels in the liver, serum iron (.micro.g/mL) and % reticulocytes (immature red blood cells) were measured as endpoints. The results are shown in FIGS. 5a-5c.

As shown in FIG. 5, in this study using the turpentine mouse model of chronic anemia, erythropoietin treatment decreased liver hepcidin mRNA expression and serum iron levels and increased reticulocyte counts. Administration of the antisense oligonucleotide targeted to hepcidin caused decreased liver hepcidin mRNA, but an increase in serum iron. Administration of an antisense oligonucleotide targeted to hepcidin in addition to erythropoietin resulted in a further increase in reticulocyte counts compared to erythropoietin treatment alone. Thus, the effects of erythropoietin and the antisense compound targeted to hepcidin were additive. These results show that treatment with both erythropoietin and an antisense compound targeted to hepcidin is effective in improving endpoints of chronic anemia in a mouse model for hypoferremia and anemia associated with inflammation.

It is contemplated herein that a further experiment, evaluating the effectiveness of combination therapy for treating anemia or increasing red blood cells could be performed, according to the methods and using the mouse model described above, by evaluating multiple experimental mice groups.

In such an experiment, a control group would receive only saline. Experimental groups would all receive turpentine. A first experimental group would receive only turpentine (no treatment or therapy). A second experimental group would receive erythropoietin treatment continuously, meaning regularly, for over a week, prior to receiving antisense compound targeted to hepcidin, and would continue to receive erythropoietin treatment throughout the treatment period with antisense compound. Thus, this second experimental group will have been receiving erythropoietin therapy prior to administration of the antisense compound. Erythropoietin therapy treatment regimens are well known in the art. Thus, in the second experimental group, the antisense compound and the erythropoietin would be administered in separate formulations, at distinct timepoints. A third experimental group would have received erythropoietin therapy at some time prior to receiving antisense compound. A fourth experimental group would receive erythropoietin therapy and antisense compound treatment simultaneously. Thus, in this group, the group would begin erythropoietin therapy simultaneously with the administration of the antisense compound. In this case, the two treatments could be administered in separate formulations or in single formulations. A fifth experimental group would receive antisense compound prior to erythropoietin therapy. Thus, the second through fifth experimental groups would be receiving a combination therapy, wherein they would receive antisense compound and be further receiving erythropoietin. A sixth experimental group would receive only erythropoietin. A seventh experimental group would receive only antisense compound.

It is further contemplated that a combination therapy method could be used for preventing, treating or ameliorating anemia or for increasing red blood cell counts in a patient. It is contemplated that this combination method could include administration of an antisense compound targeted to hepcidin and an ESA. It is contemplated that the ESA used in such a therapy could be erythropoietin, recombinant human erythropoietin, EPOGEN or PROCRIT. It is further contemplated that such a combination therapy method could comprise administration of the antisense compound and erythropoietin simultaneously. Alternatively, administration of the erythropoietin and antisense compound could be done at distinct timepoints.

If administered simultaneously, the antisense compound and erythropoietin could be given in a single formulation, or in separate formulations. Also, this combination therapy could be used to treat a patient who is receiving erythropoietin. The patient could be receiving erythropoietin prior to initiation of the combination therapy, or the patient could begin receiving the erythropoietin at the same time the combination therapy is initiated.

It is contemplated that an antisense compound used in this therapy could be an antisense oligonucleotide targeted to a nucleic acid molecule encoding hepcidin. Alternatively, the antisense compound could be double stranded. It is contemplated that the double stranded antisense compound could be an siRNA.

What is claimed is:

1. A method of inhibiting the expression of hepcidin in cells or tissues comprising contacting said cells or tissues with a compound comprising a modified oligonucleotide consisting of 12 to 35 linked nucleosides and having a nucleobase sequence comprising at least 8 contiguous nucleobases complementary to an equal length portion of nucleotides 442 to 541 of SEQ ID NO: 1, wherein said modified oligonucleotide specifically hybridizes to said nucleic acid encoding hepcidin, and wherein expression of hepcidin is inhibited.

2. The method of claim 1, wherein said compound consists of a single-stranded modified oligonucleotide.

3. The method of claim 2, wherein the nucleobase sequence of the modified oligonucleotide is 100% complementary to at least a 20 nucleobase portion of nucleotides 442 to 541 of SEQ ID NO: 1.

4. The method of claim 2, wherein at least one internucleoside linkage of said modified oligonucleotide is a modified internucleoside linkage.

5. The method of claim 4, wherein each internucleoside linkage of said modified oligonucleotide is a phosphorothioate internucleoside linkage.

6. The method of claim 2, wherein at least one nucleoside of said modified oligonucleotide comprises a modified sugar.

7. The method of claim 6, wherein at least one modified sugar is a bicyclic sugar.

8. The method of claim 6, wherein at least one modified sugar is selected from the group consisting of a 2'-O-(2-methoxyethyl), and a $(CH_2)_n$—O-2' bridge, wherein n is 1 or 2.

9. The method of claim 2, wherein at least one nucleoside of said modified oligonucleotide comprises a modified nucleobase.

10. The method of claim 9, wherein said modified nucleobase is a 5-methylcytosine.

11. The method of claim 1, wherein said modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

12. The method of claim 11, wherein said modified oligonucleotide comprises:
a gap segment consisting often linked deoxynucleosides;
a 5' wing segment consisting of five linked nucleosides;
a 3' wing segment consisting of five linked nucleosides;
wherein the gap segment is positioned between the 540 wing segment and the 3' wing segment, wherein each nucleoside of each wing segment comprises a 2'-O-methoxyethyl sugar; wherein each cytosine in said modified oligonucleotide is 5-methylcytosine, and wherein each internucleoside linkage of said modified oligonucleotide is a phosphorothioate linkage.

13. The method of claim 12, wherein said modified oligonucleotide consists of 20 linked nucleosides.

14. The method of claim 1, wherein said compound is in a composition comprising said compound or a salt thereof and a pharmaceutically acceptable carrier or diluent.

15. The method of claim 14, wherein said compound consists of a single-stranded modified oligonucleotide.

16. The method of claim 14, wherein said modified oligonucleotide consists of 20 linked nucleosides.

17. A method comprising administering to an animal a compound comprising a modified oligonucleotide consisting of 12 to 35 linked nucleosides and having a nucleobase sequence comprising at least 8 contiguous nucleobases complementary to an equal length portion of nucleotides 442 to 541 of SEQ ID NO: 1, wherein said modified oligonucleotide specifically hybridizes to said nucleic acid encoding hepcidin, and wherein expression of hepcidin is inhibited.

18. The method of claim 17, wherein the animal is a human, and said nucleobase sequence encoding hepcidin encodes human hepcidin.

19. The method of claim 18, wherein administering the compound treats a disease or condition associated with hepcidin.

20. The method of claim 19, wherein said disease or condition is selected from the group consisting of anemia, anemia of chronic disease and low serum iron level.

21. The method of claim 18, further comprising administering a erythropoiesis stimulating agent.

22. The method of claim 21, wherein said erythropoiesis stimulating agent is erythropoietin.

23. The method of claim 21, wherein said compound and said erythropoiesis stimulating agent are administered concomitantly.

24. The method of claim 18, wherein the administering is by injection.

25. A method comprising identifying a human with a disease or condition associated with hepcidin and administering to said human a therapeutically effective amount of a composition comprising a modified oligonuelcotide consisting of 12 to 35 linked nucleosides and having a nucleobase sequence comprising at least 8 contiguous nucleobases complementary to an equal length portion of nucleotides 442 to 541 of SEQ ID NO: 1, wherein said modified oligonucleotide specifically hybridizes to said nucleic acid encoding hepcidin, and wherein expression of hepcidin is inhibited.

26. The method of claim 25, wherein said disease or condition is selected from the group consisting of anemia, anemia of chronic disease and low serum iron level.

27. The method of claim 25, wherein the treatment improves a marker of said disease or condition selected from the group consisting of serum iron level, red blood cell count, hemoglobin level, hematocrit level, and reticulocyte count.

28. The method of claim 25, further comprising administering a erythropoiesis stimulating agent.

29. The method of claim 28, wherein said erythropoiesis stimulating agent is erythropoietin.

30. The method of claim 28, wherein said compound and said erythropoiesis stimulating agent are administered concomitantly.

* * * * *